(12) United States Patent
Goyal et al.

(10) Patent No.: US 8,158,139 B2
(45) Date of Patent: Apr. 17, 2012

(54) TOPICAL GEL FORMULATION COMPRISING ORGANOPHOSPHATE INSECTICIDE AND PREPARATION THEREOF

(75) Inventors: Sandhya Goyal, Ryebrook, NY (US); Subhas Kundu, Tappan, NY (US); Daniel Moros, Latchmont, NY (US); Howard Rutman, New York, NY (US); Avraham Yacobi, Englewood, NJ (US)

(73) Assignee: Taro Pharmaceuticals North America, Inc., Grand Cayman (KY)

( * ) Notice: Subject to any disclaimer, the term of this patent is extended or adjusted under 35 U.S.C. 154(b) by 1029 days.

(21) Appl. No.: 11/351,188

(22) Filed: Feb. 9, 2006

(65) Prior Publication Data

US 2007/0065474 A1   Mar. 22, 2007

Related U.S. Application Data

(63) Continuation-in-part of application No. 11/179,719, filed on Jul. 12, 2005, now Pat. No. 8,012,498.

(60) Provisional application No. 60/587,291, filed on Jul. 12, 2004, provisional application No. 60/645,781, filed on Jan. 21, 2005, provisional application No. 60/646,826, filed on Jan. 25, 2005.

(51) Int. Cl.
*A01N 57/10* (2006.01)
*A01N 57/12* (2006.01)
*A01N 25/02* (2006.01)
*A61K 9/08* (2006.01)
*A61K 31/661* (2006.01)
*A61K 47/10* (2006.01)
*A61K 47/14* (2006.01)
*A61P 33/14* (2006.01)

(52) U.S. Cl. ............... 424/405; 514/122; 514/786

(58) Field of Classification Search .............. None
See application file for complete search history.

(56) References Cited

U.S. PATENT DOCUMENTS 2,578,652 A    12/1951 Cassaday
(Continued)

FOREIGN PATENT DOCUMENTS

EP   0251464 A2   1/1988
(Continued)

OTHER PUBLICATIONS

Ovide (Malathion) Lotion, 0.5%, NDC 51672-5276-4, Jul. 2005.*
(Continued)

*Primary Examiner* — Ernst Arnold
*Assistant Examiner* — Christopher R Lea
(74) *Attorney, Agent, or Firm* — Venable LLP; Michael A. Gollin; Zayd Alathari

(57) ABSTRACT

The present invention provides a topical gel pharmaceutical formulation of insecticide suitable for treating an ectoparasite in a mammal, comprising: a) about 0.1-10% by weight of an insecticide; b) at least about 75% by weight of an organic solvent selected from the group consisting of a lower alkyl alcohol, a ketone, a glycol and a mixture thereof, wherein the organic solvent contains at least about 40% by weight of the lower alkyl alcohol; and c) at least one polymer selected from the group consisting of a cellulosic polymer, acrylates, methacrylates, and polyvinyl pyrrolidone. The present topical formulations encompass a non-flammable solvent for malathion effective in killing head lice. The present gel pharmaceutical formulation preferably contains malathion and optionally contains isopropyl myristate. The present invention further provides a process of preparing as well as a method of treating ectoparasites in a mammal using the same.

17 Claims, 3 Drawing Sheets

U.S. PATENT DOCUMENTS

| | | | |
|---|---|---|---|
| 2,879,284 A | 8/1958 | Divine et al. | |
| 2,863,902 A | 12/1958 | Santay | |
| 2,931,825 A | 4/1960 | Lutz | |
| 2,962,521 A | 11/1960 | Usui | |
| 2,980,723 A | 4/1961 | Frank et al. | |
| 3,309,432 A | 3/1967 | English | |
| 3,352,664 A | 11/1967 | Nolan et al. | |
| 3,396,223 A | 8/1968 | Stark, Jr. | |
| 3,403,201 A | 9/1968 | Adrian et al. | |
| 3,440,305 A | 4/1969 | Divine | |
| 3,463,841 A | 8/1969 | Backlund et al. | |
| 3,470,272 A | 9/1969 | Melton | |
| 3,515,782 A | 6/1970 | Nolan | |
| 3,714,301 A | 1/1973 | Thomsen | |
| 4,049,755 A | 9/1977 | Bianchi et al. | |
| 4,367,180 A | 1/1983 | Rouy et al. | |
| 4,520,013 A | 5/1985 | Nezat | |
| 4,681,964 A | 7/1987 | Annarelli et al. | |
| 5,783,202 A | 7/1998 | Tomlinson et al. | |
| 6,103,248 A | 8/2000 | Burkhart et al. | |
| 6,121,478 A | 9/2000 | Pedersen | |
| 6,280,729 B1 | 8/2001 | Huang et al. | |
| 6,500,994 B1 | 12/2002 | Brosch et al. | |
| 6,521,762 B2 | 2/2003 | Keri et al. | |
| 6,524,602 B1 | 2/2003 | Burkhart et al. | |
| 6,562,363 B1 | 5/2003 | Mantelle et al. | |
| 6,596,291 B2 | 7/2003 | Bell | |
| 6,607,716 B1 | 8/2003 | Smith et al. | |
| 6,689,394 B2 | 2/2004 | Van Scoik et al. | |
| 6,806,292 B2 * | 10/2004 | Riebel et al. | 514/609 |
| 6,939,715 B2 | 9/2005 | Beck et al. | |
| 8,012,498 B2 | 9/2011 | Goyal et al. | |
| 2002/0009486 A1 | 1/2002 | Godbey | |
| 2002/0048558 A1 | 4/2002 | Niemiec et al. | |
| 2003/0036530 A1 | 2/2003 | Bessette | |
| 2003/0040504 A1 | 2/2003 | Gans et al. | |
| 2004/0024052 A1 | 2/2004 | Gyuricza et al. | |
| 2005/0031547 A1 * | 2/2005 | Tamarkin et al. | 424/45 |
| 2006/0121073 A1 | 6/2006 | Goyal et al. | |

FOREIGN PATENT DOCUMENTS

| | | |
|---|---|---|
| FR | 1541883 | 10/1968 |
| GB | 834814 | 5/1960 |
| GB | 2204243 | 11/1988 |
| GB | 2222949 | 3/1990 |
| WO | WO 0189503 A1 * | 11/2001 |
| WO | WO-0189503 A1 | 11/2001 |
| WO | WO 03066009 A1 * | 8/2003 |
| WO | WO-2006017232 | 2/2006 |
| WO | WO-2006017263 | 2/2006 |

OTHER PUBLICATIONS

Stability Results for Malathion Lotion, Aug.-Nov. 2004.
Certificates of Analysis, malathion USP, Cheminova, Jun. 1999-Oct. 2002.
Ovide (Malathion) Lotion, 0.5%, NDA 18-613, vol. 1 of 21, 1980.
Prioderm Lotion NDA 18-613, Replacement Pages, Book 1 of 3, 1980.
Ovide (Malathion) Lotion, 0.5%, NDC 99207-650-2, p. 3-8, 2004.
Picchioni et al., "Activated Charcoal vs. "Universal Antidote" as an Antidote for Poisons," Toxicology and Applied Pharmacology, vol. 8, pp. 447-454, 1966.
Imamura et al., "Malathion and Phenthoate Carboxylesterase Activities in Pulmonary Alveolar Macrophages as Indicators of Lung Injury," Toxicology and Applied Pharmacology, vol. 70, pp. 140-147, 1983.
Rodgers et al., "Effect of administration of malathion for 90 days on macrophage function and mast cell degranulation," Toxicology Letters, vol. 93, pp. 73-82, 1997.
Umetsu et al., *J. Agric. Food Chem.*, 25: 946-953 (1977).
Aldridge et al., *Archives Toxicology*, 42: 95-106 (1979).
S. Bradu et al., "Flammability of Topical Agents to Common Environmental Fire Hazards", Ab#155-04, Mar. 2005.
International Search Report issued for PCT Applciation PCT/US06/26251, mailed on Nov. 21, 2007.
Written Opinion issued for PCT Application PCT/US06/26251, mailed on Nov. 21, 2007.
"Determination of minor components in technical Malathion", Cheminova Analyical Methods, edition 1, Jul. 1, 2003.
Cheminova, "Formulations and Brands", <http://www.cheminova.com/en/insectices/fyfanon/formulations and brands.htm>, 1 page, printed Aug. 26, 2005.
Cheminova, "Background—Fyfanon®", <http://www.cheminova.com/en/insectices/fyfanon/background.htm>, 1 page, printed Aug. 26, 2005.
"Attorney for Medicis manufacturer, of Malathion based Ovide—who writes below that USP grade Malathion is safe, effective and nontoxic", http://ww.safe2use.com/ca-ipm/00-11-28-ltr.htm, printed Oct. 6, 2005.
"Insecticides Used as Ectoparasiticides", Goodman & Gilman's "The Pharmacological Bases of Therapeutics", $9^{th}$ Ed., Copyright 1996 McGraw-Hill Companies, Inc., printed May 2, 2003.
Ovide (Malathion) Lotion, 0.5%, NDA 18-613, vol. 2, Dec. 31, 1998.
Office Action issued by the USPTO on Oct. 21, 2008 for U.S. Appl. No. 11/427,863.
Office Action issued by the USPTO on Apr. 16, 2009 for U.S. Appl. No. 11/179,924.
Nature's Mist, Skin Functioning and Dehydration, www.naturesmist.com, p. 1-4, 2003.
"A modern scourge parent scratch their heads over lice," Consumer Resorts, Feb. 1998.
Office Action issued by the USPTO on Feb. 18, 2009 for U.S. Appl. No. 11/179,719.
"Impurities of maldison," Review Scope Document Maldison, p. 6-11, Feb. 2003.
EPA 1600 Methods, p. 213, 2003.
EPA 8000 Methods, pp. 238-239, 2003.
"Occupational Exposure to Organophosphate and Carbamate Insecticides." Department of Health and Human Services, p. 1-5, pre-2003.
Subpart II. B. Pharmacology and Toxicology, p. 62-123, pre-2003.
"Malathion Reregistration Eligibility Document: Environmental Fate and Effects Chapter," United States Environmental Protection Agency, p. 1-52, 2004.
Memorandum: EFED's Response to Docket Comment, United States Environmental Protection Agency, p. 1-26, 2000.
WHO Specifications and Evaluations for Public Health Pesticides: Malathion, World Health Organization, 2003.
Health Risk Assessment of Malathion Coproducts in Malathion-Bait Used for Agricultural Pest Eradication in Urban Areas, Report of the California Environmental Protection Agency, 1997.
Keadtisuke et al., *Toxicology Letters*, 52: 35-46 (1990).
Rodgers et al., *Immunopharmacology*, 17: 131-140 (1989).
Berkman et al., "Synthesis of Chrial Malathion and Isomalathion", *Terahedron Letters*, 33(11):1415-1418 (1992).
Imamura et al., *Pharmacology and Therapeutics*, 38(3): 419-427 (1988).
Lahti et al., *Contact Dermatitis*, 12(3): 139-140 (1985).
Cotham We Jr., et al., *Food Chem*, 37: 824-828 (1989).
N. Lee Wolfe et al., *J. Agric. Food Chem.*, 23(6): 1212-1215 (1976).
P. Boutsiouki et al., "Effects of local blood flow on the percutaneous absorption of the organophosphorus compound malathion: a microdialysis study in man.", *Arch. Toxicology*, 75(6): 321-8 (2001). PubMed Abstract, http://eresources.library.mssm.edu:2115/entrez/query.fcgi?CMD=Text&DM=pubmed, 1 page.
F. Musshoff et al., "Simple determination of 22 organophosphorous pesticides in human blood using headspace solid-phase microextraction and gas chromatorgrphy with mass spectrometric detection", *Chromatogr. Sci.*, 40(1): 29-34 (2002). PubMed Abstract, http://eresources.library.mssm.edu:2115/entrez/query.fcgi?CMD=Text&DB=pubmed, 1 page.
M. Bouchard et al., *Toxicological Sciences*, 73: 182-194 (2003).
S. Padilla et al., Journal of Toxicology and Environmental Health, Part A, 67: 1477-1489 (2004).
P. Lee et al., *Intensive Care Med.*, 27: 694-699 (2001).
R. Zweiner et al., *Pediatrics*, 81(1): 121-126 (1988).
C. Vidair, Toxicology and Applied Pharmacology, 196: 287-302 (2004).

D. Hamilton, "JMPS Evaluation of Data Supporting Specification—the Practicalities", CIPAC Symposium, Utrecht, 8 pages. (Jun. 6, 2005).
M. Fuller, "Jun. 28, 1998—Bradenton Mediterranean Fruit Fly Update DACS", http://pestalert.ifas.ufl.edu/Medfly/dacs06228.htm (accessed Nov. 13, 2005).
W. Boyes et al., *Journal of Applied Toxicology*, 19: 473-483 (1999).
J. Cocker et al., *Toxicology Letters*, 134: 97-103 (2002).
M. Maroni et al., *Toxicology*, 143: 5-37 (2000).
M. Brown et al., *Environ. Sci. Technol.*, 27(2): 388-397 (1993).
R. Baselt et al.,"Malathion", *Disposition of Toxic Drugs and Chemicals in Man*, p. 475-478, 1989.
R. Krieger et al., *Arch. Environ. Contam. Toxicol.*, 38: 546-553 (2000).
J. Storm et al., *Toxicology*, 150: 1-29 (2000).
B. Nutley et al., *Pestic. Sci.*, 38: 315-322 (1993).
R. Fenske et al., *J. Agric. Food Chem.*, 37: 995-998 (1989).
K. Rodgers et al., *Pesticide Biochemistry and Physiology*, 25: 358-365 (1986).
J. Herath et al., *Cytologia*, 54: 191-195 (1989).
A. Nishio et al., Journal of Toxicology and Environmental Health, 8: 939-946 (1981).
Z. Walter et al., *Human Genetics*, 53: 375-381 (1980).
P. Flessel et al., *Environmental and Molecular Mutagenesis*, 22: 7-17 (1993).
S. Amer et al., Journal of Applied Toxicology, 16(1): 1-3 (1996).
V. Garry et al., Teratogenesis, Carcinogenesis, and Mutagenesis, 10: 21-29 (1990).
A. Nicholas et al., Mutation Research, 67: 167-172 (1979).
FAO Specifications and Evaluations for Agricultural Pesticides, Malathion, Food and Agricultural Organization of the United States, Dec. 2004.
Talley, Todd T. "My Research", http://www2.umt.edu/medchem/ttt/research%20page.html, printed on Nov. 13, 2005.
Malathion, monograph numbe 5740, copyright 1999 by Merck & Co., Inc., Whitehouse Stations, NJ, USA.
"Malathion vs. Mosquitoes", CBC Manitoba, http://winnipeg.cbc.ca/indepth/malathion/, 3 pages, Jul. 7, 2004, printed Dec. 14, 2004.
"Pesticides: Topical & Chemical Fact Sheet; Malathion for Mosquito Control", U.S. Environmental Protection Agency, http://www.epa.gov/pesticides/factsheets/malathion4mosquitos.htm, 5 pages, updated Apr. 17, 2002, printed Dec. 14, 2004.
"Malathion—toxicity, ecological toxicity and regulatory information", PAN Pesticides Database—Chemicals, http://www.pesticidenfo.org/Detail_Chemical.jsp?Rec_Id=PC32924, 9 pages, printed Aug. 31, 2005.
"I.A. Reference Dose for Chronic Oral Exposure (RfD): Substance Name—Malathion", 1 page, Last Revised Jan. 1, 1992.
Sigma-Aldrich, "Product Name: Malathion", http://www.sigmaaldrich.com/cgi-bin/hsrun/Distributed/HahtShop/HahtShop.htx;start=frmCa....., 1 page, printed Oct. 9, 2003.
Chemservice, "Detailed Database Results, Description: Malathion", http://www.chemservice.com/result_detail.asp?CATNUM=F2118, 2 pages, printed Oct. 7, 2003.
"Malathion", IARC Summaries & Evaluations, vol. 30, 1983, http://www.inchem.org/documents/iarc/vol30/malathion.html, 4 pages, printed Jul. 11, 2005.
"Maldison (Malathion) Review Scope Document", National Registration Authority for Agricultural and Veterinary Chemicals, Feb. 2003.
"Joint Statement on Review of Malathion", Department of Health, http://www.doh.gov.uk/com/malathion.htm, p. 1-16, Mar. 2003, printed on Oct. 7, 2003.
"COM meeting Apr. 25, 2002", Department of Health, http://www.doh.gov.uk/com/mut023.htm, p. 1-8, printed on Oct. 6, 2003.
"Guidelines for Physicians who supervise workers exposed to cholinesterase-inhibiting pesticides", 4th Ed., Office of Environmental Hazard Assessment California Environmental Protection Agency, 2002.
Meinking et al., Pediatric Dermatology, vol. 21, No. 6, pp. 670-674, 2004.
Office Action issued by the USPTO on Sep. 16, 2009 for U.S. Appl. No. 11/179,719.
Office Action issued by the USPTO on Sep. 24, 2009 for U.S. Appl. No. 11/179,924.
Office Action mailed by U.S. Patent and Trademark Office for U.S. Appl. No. 11/179,241 on Jun. 6, 2011.
Office Action issued by USPTO for U.S. Appl. No. 11/179,719 on May 27, 2010.
Office Action issued by USPTO for U.S. Appl. No. 11/179,924 on Mar. 16, 2010.
Delphion, ((malathion)<in>Claims)—Aug. 25, 2006.
Delphion—((impurit* and detect* and purifica*) <in> CLAIMS))—Aug. 25, 2006.
Reimschussel et al., "Radioisotopic Studies on the Content and Conversion Rates of Toxic Impurities in Malathion," Pesticides: food and environmental implications, Proceedings of a symposium held in Neuherberg, Nov. 24-27, 1987, pp. 301-303, Published 1988. (Abstract Only).
Toia et al., "Identification and Toxicological Evaluation of Impurities in Technical Malathion and Fenthion," J. Agric. Food Chem., vol. 28, No. 3, pp. 599-604, 1980. (Abstract A Only).
Makarova et al., "Photometric Determination of Organophosphorus Pesticides After Separation By Thin Layer Chromatography," Indust. Lab., vol. 40, No. 7, pp. 961-964, 1974. (Abstract Only).
Liu et al., "Rapid Isolation with Sep-Pak C18 Cartridges and Wide Bore Capillary Gas Chromatography of Organophosphate Pesticides," Forensic Science International, vol. 41, No. 1-2, pp. 67-72, 1989. (Abstract Only).
Imamura et al., "Pulmonary Toxicity of Phosphorothioate Impurities Found in Organophosphate Insecticides," Pharmacology and Therapeutics, vol. 38, No. 3, pp. 419-427, 1988. (Abstract Only).
Talcott et al., "Inactivation of Esterases by Impurities Isolated from Technical Malathion," Toxicology and Applied Pharmacology, vol. 49, No. 1, pp. 107-112, 1979. (Abstract Only).
Umezu, "Toxicity of Malathion to Mammals Potentiation of Toxicity by Impurities," Kagaku To Seibutsu (Chem. Biol.) vol. 16, No. 5, pp. 302-304, 1978. (English Abstract Only).
Malathion, Pestanal®, analytical standard, Sigma-Aldrich Catalog, 2006, with Certificate of Analysis.
Blasiak et al., "In Vitro Studies on the Genotoxicity of the Organophosphorus Insecticide Malathion and Its Two Analogues," Mutat. Res., vol. 445, No. 2, pp. 275-283, 2003. (Abstract Only).
Wilkins et al., "A Study of the Trans-Esterification Products of Malathion by Capillary Gas Chromatography-Mass Spectrometry," Pesticide Science, vol. 20, No. 4, pp. 259-270, 1987. (Abstract Only).
Baker, Jr. et al., Epidemic Malathion Poisoning in Pakistan Malaria Workers, The Lancet, vol. 1, No. 8054, 1978.
USP Monographs: Malathion Lotion, 2008.
USP Monographs: Malathion, 2008.
Patel et al., "Manufacture of Malathion," Pestic., Symp. (1968), Meeting Date 1964, pp. 69-72. (Abstract Only).
Shvetsova-Shilovskaya et al., "Purification of Technical Carbophos," Khimicheskaya Promyshlennost, vol. 47, No. 11, p. 869, 1971. (English Abstract Only).
Lupea et al., "Addition of Dimethyl Dithiophosphate to Ethyl Maleate and Ethyl Fumarate," Buletinul Stiintific si Tehnic al Institutului Politechnic Traian Vuia Timisoara, Seria Chimie, vol. 26, No. 1, pp. 51-60, 1981. (English Abstract Only).
Polec et al., "Synthesis of Malathion Enantiomers," Organika, vol. date 1995, pp. 7-15, 1996. (English Abstract Only).
Polec et al., "Simple Syntheses of Malathion and Malaoxon Enantiomers, and Isomalathion Diastereoisomers: Toxicity-Configuration Relationship," Pesticide Science, vol. 53, No. 2, pp. 165-171, 1998. (Abstract Only).
Al-Wakil et al., "Separation and Preconcentration of Malathion and Azamethiphos by Unloaded Polyurethane Foams," Qatar University Science Journal, vol. 14(spec. issue), 1994. (Abstract Only).
Retro Search, Malathion Impurities, Sep. 13, 2005. (Collection of Abstracts).
Retro Search, Malathion Impurity, Sep. 13, 2005. (Collection of Abstracts).
Science IP, Preliminary Search Report 2, 2005.
Malathion, 1GM, Neat—Product No. PS86; Sigma-Aldrich Catalog, 2003; with Certificate of Analysis.

Supplementary European Search Report issued in EP Application No. 06774561 on Jun. 4, 2010.

Toia et al., "Identification and Toxicological Evaluation of Impurities in Technical Malathion and Fenthion," J. Agric. Food Chem., vol. 28, No. 3, pp. 599-604, 1980. (Abstract B Only).

Ramachandran et al., "Rheological Characterization of Hydroxypropylcellulose Gels," Drug Development and Industrial Pharmacy, vol. 25, No. 2, pp. 153-161, 1999.

Office Action issued by USPTO for U.S. Appl. No. 12/353,691 on Sep. 8, 2010.

Office Action issued by the USPTO on Nov. 26, 2010 for U.S. Appl. No. 11/179,924.

Office Action issued by the USPTO on Nov. 28, 2011 for U.S. Appl. No. 11/179,924.

Meinking et al., "Comparative In Vitro Pediculicidal Efficacy of Treatments in a Resistant Head Lice Population in the United States," Arch. Dermatol. vol. 138, pp. 220-224, 2002.

Matousek et al., "Evaluation of the effect of pH on in vitro growth of *Malassezia pachydermatis*," The Canadian Journal of Veterinary Research, vol. 67, pp. 56-59, 2003.

Segur et al., "Viscosity of Glycerol and It's Aqueous Solutions," Industrial and Engineering Chemistry, vol. 43, No. 9, pp. 2117-2120, 1951.

Savage, "Temperature-Viscisity Relationships for Water-Soluble Cellulose Ethers," Industrial and Engineering Chemistry, vol. 49, No. 1, pp. 99-103, 1957.

Office Action issued by the USPTO for U.S. Appl. No. 13/220,935 on Feb. 15, 2012.

* cited by examiner

TOPICAL GEL FORMULATION COMPRISING ORGANOPHOSPHATE INSECTICIDE AND PREPARATION THEREOF

CROSS REFERENCE TO RELATED APPLICATIONS

This application is a continuation-in-part of Utility application Ser. No. 11/179,719 (filed Jul. 12, 2005) now U.S. Pat. No. 8,012,498, which claims the benefit under 35 U.S.C. §119(e) of Provisional Application Ser. Nos. 60/587,291 (filed Jul. 12, 2004), 60/645,781 (filed Jan. 21, 2005) and 60/646,826 (filed Jan. 25, 2005), the disclosures of which are incorporated by reference in their entireties herein.

FIELD OF THE INVENTION

The present invention generally relates to the treatment of ectoparasites such as head lice, body lice, pubic lice and scabies in a mammal. In particular, the present invention relates to a topical gel pharmaceutical formulation comprising an organophosphate insecticide such as malathion that is effective, safe and has a short application time.

BACKGROUND OF THE INVENTION

Infection with ectoparasites in humans is common and remains a major health problem in the U.S. and worldwide. The most common ectoparasites include head lice, body lice, pubic lice and scabies. For example, head lice (*Pediculus capitis*) is a persistent health problem. Six million school children in United States will become infected with head lice annually; that is, one out of every four students in elementary schools (*Consumer Reports*, February 1998). A total of about ten million people will be infected when all ages are accounted. The incidence of head lice is only slightly improved from the reported incidence in 1940, which was prior to the advent of insecticides and superior knowledge by the medical establishment.

Infestation with head lice in human typically causes itching and lesion of the scalp, as well as swelling of glands in the neck or under the arms. A secondary problem is that many schools have enforced absenteeism if a child has any nits (lice eggs) in their hair (See, e.g., U.S. Pat. No. 6,103,248). Such a "no-nit" policy has negative social implications for the child and the parents. Head lice is becoming a sensitive social issue. Evidence also strongly supports that head lice could be vectors for systemic human infections. For example Rickettsiae and Spirochetes are known to be obtainable from the blood of the host (head lice are blood suckers like mosquitoes); these organisms multiply in the gut of the head lice, and are found in high numbers in their feces (See, e.g., U.S. Pat. No. 6,103,248). Viruses, like the AIDS virus, have been found in the gut and feces of head lice (See, e.g., U.S. Pat. No. 6,103,248).

Body lice are tiny parasitic insects (*Pediculus humanus corporis*) that can be spread by close contact with infected people or clothing. They feed on human blood, lay eggs and deposit their fecal matter on skin. Infestation with body lice in humans causes intense itching. When body lice are not feeding on blood, they live in the seams and folds of clothing. Pubic lice are parasitic insects found commonly in the genital area, body hair including hair on the legs, armpit, mustache, eyebrows and eyelashes in humans, especially in young children.

Scabies is caused by a tiny mite (called Human Itch mite) that has infested humans for at least 2,500 years. Scabies can barely be seen by the human eyes. Dermatologists estimate that more than 300 million cases of scabies occur worldwide every year. The condition can strike anyone of any race or age, regardless of personal hygiene. Within several weeks, the patient develops an allergic reaction causing severe itching; often intense enough to keep sufferers awake all night.

Home remedies for these ectoparasites are largely ineffective or inconvenient to apply. For example, remedies against head lice include applying petroleum jelly or mayonnaise on the scalp. Unfortunately, these treatments are ineffective. Commercial treatments also include applying an insecticide on the scalp hair. The marketed products (prescription and OTC) include insecticides such as malathion, gamma benzene hexachloride, permethrin, pyrethrin, or piperonyl butoxide.

These pharmaceutically formulated insecticides are universally admixed in a water based composition such as mousse, foam, ointment, shampoo, lotion, and cream rinse. U.S. Pat. No. 5,783,202 describes a mousse formulation and European Patent 125471 describes a foaming pesticide. These two formulations are limited as they break down quickly (e.g., within 2-30 seconds) and risking the exposure of eyes/ears to the toxic insecticide. In addition, the generated air bubbles in these formulations may be bigger than the pores on the cap of the eggs and hence may actually impede the insecticide activity. U.S. Pat. No. 6,524,602 describes the use of N,O-carboxymethyl-chitosan polymer to increase the retention of formulation on skin. The safety of the polymer and how it affects stability of insecticides have not been established.

U.S. Pat. No. 6,103,248 describes a thick ointment preparation containing an insecticide, lipophillic carrier and a surfactant. The carrier has a viscosity within the range of 10,000 centipoise to about 85,000 centipoise at 21° C. A main disadvantage associated with such formulations is the presence of surfactant, which may raise the pH of the formulation thus affecting the stability of insecticides like malathion which is pH sensitive. Because of its high viscosity and oily nature, the formulation is difficult to spread evenly in the hair, and to wash away from the hair (requires a minimum of two washings). Some head lice products are available as shampoo; however the efficacy of such dosage form is uncertain. The shampoo needs to be diluted with water to 1:20 to 1:30 times for application to the hair which lowers the efficacy of the insecticide. Head lice have spiracles, by which the adult lice breathe and the eggs have opercula by which lice larvae in the eggs exchange oxygen. When lice comes in contact with water, it grasps hair reflectively and close their breathing spiracles to avoid being drowned. The opercula in eggs also close when in contact with water thus making it difficult for shampoos and other aqueous products containing insecticide difficult to penetrate and lead to loss in efficacy. Aqueous lotions, shampoos and cream rinse also have too big a wetting angle for fluid to flow into the opercula directly. Because of these problems associated with various formulations, there has been an increasing evidence of development of resistance against these products.

Currently marketed Ovide® Lotion containing malathion, is the only insecticide, against which the lice has still not developed resistance. Since its introduction in the mid 1980's, there are no other commercial malathion preparations other than the lotion form. The pharmaceutical form of malathion contains 78% isopropyl alcohol, which functions as a solvent for delivery of malathion. A major difficulty encountered in applying this lotion is that it spreads freely on the scalp and hair shafts, thus giving false appearance of sufficient wetness after application of very small quantity (i.e., patients get the impression that this quantity is sufficient). Moreover, the lotion (due to its low viscosity) may easily run into the eyes, ears and down the patient's neck causing eye, ear and skin irritation as well as soiling the clothes. The patient is instructed to apply the lotion for 8-12 hours and not go near open flame or use a hair dryer during this time due to higher alcohol content which is flammable.

Treatment against ectoparasites further includes applying permethrin cream (5%), pyrethrin shampoo, lindane (1%) lotion, crotamiton cream, or oral dosage of ivermectin. Permethrin and lindane treatment requires applying the drugs from the neck down at night and washed off in the morning. Reapplication is often required. Many of these drugs are either toxic to nervous system or causes allergy. For example, lindane can not be used on infants, children, pregnant/nursing women, people with seizures or other neurological diseases. The National Pediculosis (head lice) Association recently established a database to track "adverse event" reports related to use of lindane to treat head lice in the U.S. In the first 24 months, more than 500 events were reported (County Sanitation Districts 2000). In 1996, in response to a petition from several public interest groups in the U.S., the Food and Drug Administration reviewed its regulations and determined that lindane should be used only as a "treatment of last resort" for lice and scabies. Lindane 1% shampoo is banned in California due to environmental problems with lindane in sewage effluent. Crotamiton cream has allergic activity. Oral dosage of ivermectin cannot to be used in infants or pregnant women. Antihistamines often are needed to relieve itching for the treatment.

Thus, there is a continuing need for a pharmaceutical formulation containing stable insecticides including organophosphate insecticides, such as malathion, that are effective, safe and have a short application time.

SUMMARY OF THE INVENTION

In one aspect, the present invention provides a topical gel pharmaceutical formulation comprising an insecticide effective to exhibit pediculicidal, ovicidal and scabicidal activity, an organic solvent and a viscosity-modifying polymer.

In another aspect, the present invention provides a topical gel pharmaceutical formulation comprising an organophosphate insecticide (such as malathion) effective to exhibit pediculicidal, ovicidal and scabicidal activity, an organic solvent and a viscosity-modifying polymer.

In another aspect, the present invention provides a topical gel pharmaceutical formulation comprising malathion and an organic solvent that exhibits less flammable activity.

In another aspect, the present invention provides a topical gel pharmaceutical formulation optionally containing isopropyl myristate.

In another aspect, the present invention provides a topical lotion pharmaceutical formulation comprising malathion and an organic solvent that exhibits less flammable activity. Preferably, the formulation contains about 75% by weight of a mixture of isopropyl alcohol and organic solvent such as a glycol, or a $C_6$-$C_{12}$ triglyceride, wherein the organic solvent is at least about 35% by weight.

In another aspect, the present invention provides a process of preparing a topical gel pharmaceutical formulation, comprising the steps of:

a) mixing a viscosity-modifying polymer in an organic solvent to hydrate the polymer in the organic solvent, wherein the viscosity-modifying polymer is at least one polymer selected from the group consisting of a cellulosic polymer, acrylates, methacrylates, and polyvinyl pyrrolidone, wherein the organic solvent is selected from the group consisting of a lower alkyl alcohol, a ketone, a glycol and a mixture thereof, wherein the organic solvent is at least about 75% by weight, wherein the organic solvent contains at least about 40% by weight of the lower alkyl alcohol; and b) adding about 0.1-10% by weight an insecticide into the polymer mixture to form a topical gel pharmaceutical formulation.

In yet another aspect, the present invention provides a method for treating head lice in a mammal, comprising the step of topically applying to the mammal in need thereof, a therapeutically effective amount of the gel pharmaceutical formulation, said gel pharmaceutical composition comprises an organophosphate insecticide (such as malathion) exhibiting pediculicidal and ovicidal activity, an organic solvent and a viscosity-modifying polymer.

DETAILED DESCRIPTION OF THE INVENTION

Figure 1:
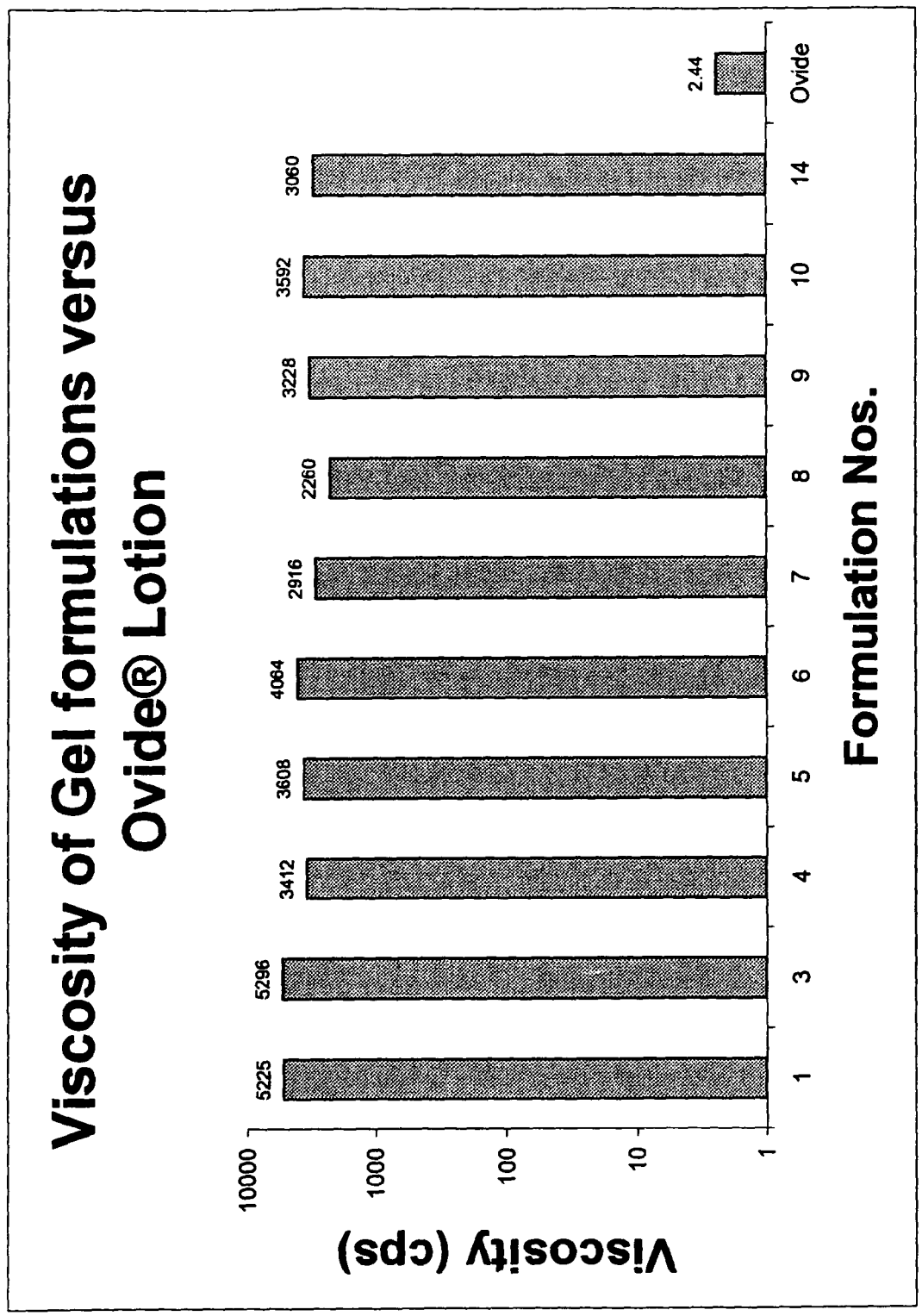
FIG. 1 depicts the viscosity of various gel formulations including Ovide® lotion.

Definitions: As used herein, "insecticide" refers to a substance used to prevent, destroy, repel, mitigate, or kill insects; "organophosphate" refers to an organophosphorous compound that displays anti-cholinesterase activity; "malathion" refers to a pesticide (CAS # 121-75-5) belonging to the category of organophosphate insecticide; "mammal" refers to a class of higher vertebrates comprising man and all other animals that nourish their young with milk secreted by mammary glands and have the skin more or less covered with hair, "pediculicidal activity" refers to lice killing activity; "ovicidal activity" refers to egg (of lice) killing activity; "scabicidal" refers to scabies mites killing activity; "HPC" refers to hydroxy propyl cellulose; "cellulosic polymer" refers to polymers containing cellulose or modified cellulose and are available in a variety of grades depending upon the viscosity and extent of crosslinking; "less-flammable" refers to a lotion or gel formulation containing less than 78% wt isopropyl alcohol such that the flash point of the resulting mixture is higher than the flash point of the formulation containing 78% wt isopropyl alcohol; flash point of the solvents was determined by a standard "closed cup" method well-known in the art. The flash points of the following solvents are: isopropyl alcohol (11.7° C.), propylene glycol (99° C.), Miglyol 812 (220° C.); terpineol (89° C.); dipentene (46° C.); ethyl alcohol (14° C.); and benzyl alcohol (100.6° C.); "lower alkyl alcohol" refers to a compound of a general formula ROH where R is linear or branched $C_{1-8}$ alkyl group (including substituted) and OH is the hydroxyl group; "ketone" refers to an organic compound with a carbonyl group attached to two carbon atoms; "glycol" refers to an organic compound containing two hydroxyl groups; "$C_6$-$C_{12}$ triglyceride" refers to a triglyceride having fatty acid chains of a carbon chain length of 6-12; "$C_8$-$C_{10}$ triglyceride" refers to a triglyceride having fatty acid chains of a carbon chain length of 8-10; "ectoparasites" refers to an organism that lives parasitically on the outside of it host e.g. insects which live on the skin of cattle like ticks, lice, fleas; "head lice" refers to *Pediculus capitis*, that are small parasitic insects exquisitely adapted to living mainly on the scalp and neck hairs of their human host; "pubic lice" refers to small, six-legged creatures that invade the genital hair region and infest it with their eggs; they can also infest armpit hair and eyebrows; "body lice" refers to tiny parasitic insects (*Pediculus humanus corporis*) that can be spread by close contact with other people; "scabies" refers to an infestation of the skin with the microscopic mite *Sarcoptes scabei*; "therapeutically effective amount" refers to an amount of drug sufficient to exert the desired therapeutic effect; "sufficient to kill" refers to amount of a therapeutically effective agent which is sufficient to kill an organism; "flash point" refers to the lowest temperature at which a liquid or a solid gives off enough vapor to form flammable air-vapor mixture near its surface; "viscosity" refers to a measure of a fluid's resistance to flow; "viscosity-modifying polymer" refers to a polymer that changes the viscosity of the formulation, preferably, a modifying polymer increases the viscosity of the formulation; "Ovide®" refers to a tradename product having the malathion as an active ingredient and is marketed by Taro Pharmaceuticals, NY, USA; "Lindane" refers to a generic name product having the gamma benzene chloride as an active ingredient and is marketed by Alpharma, NJ, USA; "Nix®" refers to a tradename product having permethrin as an active ingredient and is marketed by Warner-Lambert, Morris Plains, N.J., USA; and "Krucel HF®" refers to a tradename product having hydroxypropyl cellulose and is marketed by Hercules Incorporated, Wilmington, Del.

Unless otherwise indicated, as expressed in the present specification as well as in the set of claims, % wt refers to % wt of a specific ingredient/total wt of formulation. The term "about" is intended to encompass +/−10% of a value.

By employing the present invention, all of the prior art difficulties and drawbacks are eliminated and a safe, effective gel formulation containing stable insecticide is attained. As detailed herein, the present invention provides a gel formulation comprising an insecticide (such as malathion) which have been uniquely combined to attain a stable insecticide for highly effective insecticide activity.

For purposes of the present invention, a topical gel formulation is intended to encompass other suitable dosage forms including cream, foam and the like, so long as the viscosity of the other dosage forms is similar to that of the gel formulation as detailed herein.

Although gel preparation for insecticide has been employed, we have found surprisingly that a gel formulation for insecticide having a high alcohol content and substantially aqueous free (i.e., not a water-based formulation) is exceedingly better. Traditional gel preparation often involves the use of an aqueous base (i.e., formulation containing water) and a low level of alcohol (i.e., usually <10-20% alcohol). Aqueous base formulation that contains water is found to be unsuitable for insecticide including organophosphate compounds (e.g., malathion) due to its well-known property that organophophate compounds are unstable when exposed to an aqueous environment. Thus, the presence of water in any formulation renders the organophosphate compounds to be unstable. The use of high alcohol content and substantially aqueous-free formulation as a gel preparation represents an unique and unobvious departure from prior art teachings.

One unique aspect of the present invention is that the insecticide (such as malathion) is stable in the present formulation. The absence of water maintains the stability of the insecticide. Alkyl alcohol is maintained at an amount sufficient to effect the insecticide activity. Alkyl alcohol acts synergistically with the stable insecticides in the gel formulation to kill the ectoparasites.

Optionally, the present formulation may contain isopropyl myristate. Without being bound by a theory, it is believed that the presence of isopropyl myristate may enhance the penetration of the insecticide (such as malathion). Our data indicate that the presence of isopropyl myristate does not affect the stability of the gel formulation.

Another unique aspect of the present invention is that the gel provides an optimal viscosity such that it avoids the run-over disadvantages of the lotion. We have found surprisingly that viscosity-modifying polymer, when prepared in a substantially aqueous free formulation, provides good viscosity for easy spreading over the hair/body while maintaining stability for the insecticide (such as malathion).

Another yet unique aspect of the present invention is that the gel provides good retention (by avoiding rapid evaporation) of high alcohol level within the formulation for effective killing of lice.

In accordance with the present invention, malathion is a preferred insecticide used in the topical gel pharmaceutical formulation. Malathion is an organophosphate pesticide which members include methyl parathion, dimethoate and chlorpyrifos. Malathion was first introduced in the U.S. in 1950 by American Cyanamid Company. Malathion has a chemical name of O,O-dimethyl-S-(1,2-di(ethoxycarbonyl)-ethyl) phosphorodithioate and has a CAS No. 121-75-5. U.S. Pat. Nos. 3,352,664, 3,396,223, and 3,515,782 describe the use of malathion in killing pesticides, the disclosure of these reference is incorporated by reference.

Conventional processes for preparing malathion are well known and generally include the two-step process of reacting phosphorus pentasulfide with methanol in the presence of dioxane, benzene or toluene to form a solution of crude O,O-dimethyldithiophosphoric acid (DMDP) and then reacting the solution with diethyl maleate (See, e.g., U.S. Pat. Nos. 3,463,841 and 4,367,180). In a recently filed application (U.S. Provisional Application 60/697,010, from which priority was claimed in U.S. Ser. No. 11/427863) entitled "Process for preparing pharmaceutical grade malathion" (filed on Jul. 6, 2005), we disclosed an improved malathion composition that has a better impurity profile as well as a process of preparing a pharmaceutical grade malathion having >99% purity and an improved impurity profile (i.e., less than 0.1% isomalathion, 0.05% O,O,S-trimethyl phosphorothioate, and 0.1% methyl malathion). The disclosed process generally involves reacting a phosphorus sulfide with methanol in an organic solvent to form O,O-dimethyldithiophosphoric acid; extracting the acid in water; and reacting the O,O-dimethyldithiophosphoric acid in water with diethyl maleate to form malathion, as exemplified below. The disclosure of this recently filed application, U.S. Provisional Application 60/697,010, is hereby incorporated by reference in its entirety.

In one embodiment, the present invention provides a topical gel pharmaceutical formulation of insecticide suitable for treating an ectoparasite in a mammal, comprising:
  a) about 0.1-10% by weight of an insecticide;
  b) at least about 75% by weight of an organic solvent selected from the group consisting of a lower alkyl alcohol, a ketone, a glycol and a mixture thereof, wherein the organic solvent contains at least about 40% by weight of the lower alkyl alcohol; and c) at least one viscosity-modifying polymer selected from the group consisting of a cellulosic polymer, acrylates, methacrylates, and polyvinyl pyrrolidone.

Preferably, the insecticide is an organophosphate.

In accordance with the present invention, organophosphorus insecticides include, but are not limited to, malathion, chlorphyrifos, parathion, ethyl-methyl parathion, methyl malathion, ethion fonofos, acephate, formothion, azamethiphos, azinphos-ethyl, azinphos-methyl, chlorfenvinphos, cyanophos, danifos, fensulfothion, tribufos, dimethoate, dioxathion, disulfoton, endothion, ethion, fenitrothion, ethoprop, chlorethoxyfos, iprobenfos, isazofos, isofenphos, isoxathion, vamidothion, methidathion, methyl parathion, mevinphos, morphothion, naled, fenamiphos, fosmethilan, pyridaphenthion, omethoate, parathion, phencapton, phenthoate, phorate, phosalone, phosmet, phosnichlor, phosphamidon, leptophos, phoxim, pirimiphos-methyl, pirimiphos-ethyl, profenofos, prothidathion, prothoate, piperophos, tolclofos-methyl, ronnel, cadusafos, sophamide, demeton, demeton I (thiono isomer), demeton II (thiolo isomer), cyanthoate, tebupirimfos, terbufos, tetra chlorvinphos, thiometon, prothiofos, dialifos, trichlorfon and the like.

Preferably, the organophosphorus insecticides are malathion, phosmet, parathion, dioxanthion, terbufos and prothiofos.

More preferably, the organophosphate is malathion.

Preferably, the insecticide is gamma benzene chloride, permethrin, pyrethrin, piperonyl butoxide, spinosyns, polydimethyl siloxane or pyrantel pamoate.

Preferably, the insecticide is present in the amount of about 0.1% to about 10%. Preferably, the insecticide is present in the amount of about 0.1% to about 5%. More preferably, the insecticide is present in the amount of about 0.5%.

Preferably, the insecticide is malathion. Preferably, malathion is present in the amount of about 0.1% to about 10%. More preferably, malathion is present in the amount of about 0.1% to about 5%. More preferably, malathion is present in the amount of about 0.5%

Preferably, the organic solvent is at least one solvent exemplified to include a lower alkyl alcohol, a ketone, a glycol and the like.

Preferably, the organic solvent is present in the amount of about 1% to about 99%. More preferably, the organic solvent is present in the amount of about 20% to about 80%. More preferably, the organic solvent is present in the amount of about 60% to about 80%.

Preferably, the lower alkyl alcohol is exemplified to include a $C_1$-$C_8$ alcohol and the like, including branch or linear alcohol. Preferably, the lower alkyl alcohol is ethyl alcohol or isopropyl alcohol.

Preferably, the ketone is exemplified to include acetone, N-methyl pyrrolidone, and the like.

Preferably, the glycol is exemplified to include propylene glycol and the like.

Preferably, the organic solvent is a mixture of a first solvent selected from the group consisting of ethyl alcohol and isopropyl alcohol and a second solvent selected from the group consisting of benzyl alcohol, ketone and glycol, wherein the wt/wt ratio of the first solvent and the second solvent results in an increase in the flash point of the formulation to reduce its flammability.

Preferably, the organic solvent is a mixture of ethyl alcohol and propylene glycol, ethyl alcohol and benzyl alcohol, ethyl alcohol and N-methylpyrrolidone.

Preferably, the organic solvent is a mixture of isopropyl alcohol and propylene glycol, isopropyl alcohol and benzyl alcohol, ethyl alcohol and N-methylpyrrolidone.

Optionally, the present formulation may contain isopropyl myristate. Isopropyl myristate may be present in the amount of about 4% to about 14%. Preferably, isopropyl myristate is present in the amount of about 8% to about 12%. More preferably, isopropyl myristate is present in the amount of about 10%.

Preferably, the cellulosic polymer is exemplified to include hydroxylethyl cellulose, hydroxy propyl cellulose, hydroxy propyl methyl cellulose, methyl cellulose, carboxy methyl cellulose, sodium carboxy methyl cellulose, ethyl cellulose and the like. More preferably, the cellulosic polymer is hydroxylpropyl cellulose.

Preferably, the cellulosic polymer is present in the amount of about 0.1% to about 20%. More preferably, the cellulosic polymer is present in the amount of about 0.1% to about 10%. More preferably, the cellulosic polymer is present in the amount of about 0.5% to about 5%.

Preferably, the topical gel pharmaceutical formulation may further contain a fragrance. Preferably, the fragrance is exemplified to include terpineol, terpenes, pine needle oil and other natural and synthetic fragrances and the like.

Preferably, the fragrance is present in the amount of about 0.1% to about 30%. More preferably, the fragrance is present in the amount of about 5% to about 20%. More preferably, the fragrance is present in the amount of about 10% to about 20%.

Preferably, the topical gel pharmaceutical formulation may further contain an antioxidant. Preferably, the antioxidant is exemplified to include ascorbic acid, butylated hydroxyl anisole, butlylated hydroxy toluene, propyl gallate, tartaric acid, phosphoric acid, erythrobic acid, lactic acid, sodium sulfite, sodium bisulfate, sodium metabisulfite, thioglycolic acid, cysteine hydrochloride, alpha tocopherol and the like. The antioxidant may be present in the salt form.

Preferably, the antioxidant is present in the amount of about 0.025% to about 5%. More preferably, the antioxidant is present in the amount of about 0.1% to about 1%.

The present topical gel pharmaceutical formulation is resistant to microbial growth (due to high alcohol content) and hence does not require the addition of preservatives. However, formulations containing lower amount of alcohol may be preserved by adding preservatives that are commonly known to the one skilled in the art Preferably, the topical gel pharmaceutical formulation has a pH between about 3 to about 10. More preferably, the pH is about 4 to about 7. More preferably, the pH is about 5.

Preferably, the present pharmaceutical formulation is present as a gel. Preferably, the present pharmaceutical formulation has a viscosity of at least about 1,000 centipoise (cps). More preferably, the topical gel pharmaceutical formulation has a viscosity of the gel pharmaceutical formulation is at least about 3,000 cps. Preferably, the viscosity of the present pharmaceutical formulation does not exceed 50,000 cps.

In another embodiment, the present invention provides a topical gel pharmaceutical formulation of insecticide suitable for treating an ectoparasite in a mammal, comprising: a) about 0.5% by weight of malathion; b) at least one organic solvent selected from the group consisting of ethyl alcohol, isopropyl alcohol, propylene alcohol, benzyl alcohol, and propylene glycol; and c) hydroxylpropyl cellulose.

In another embodiment, the present invention provides a topical gel pharmaceutical formulation of insecticide suitable for treating an ectoparasite in a mammal, comprising: a) about 0.5% by weight of malathion; b) at least one organic solvent selected from the group consisting of ethyl alcohol, isopropyl alcohol, propylene alcohol, benzyl alcohol, and propylene glycol; c) isopropyl myristate; and d) hydroxylpropyl cellulose.

Figure 3:
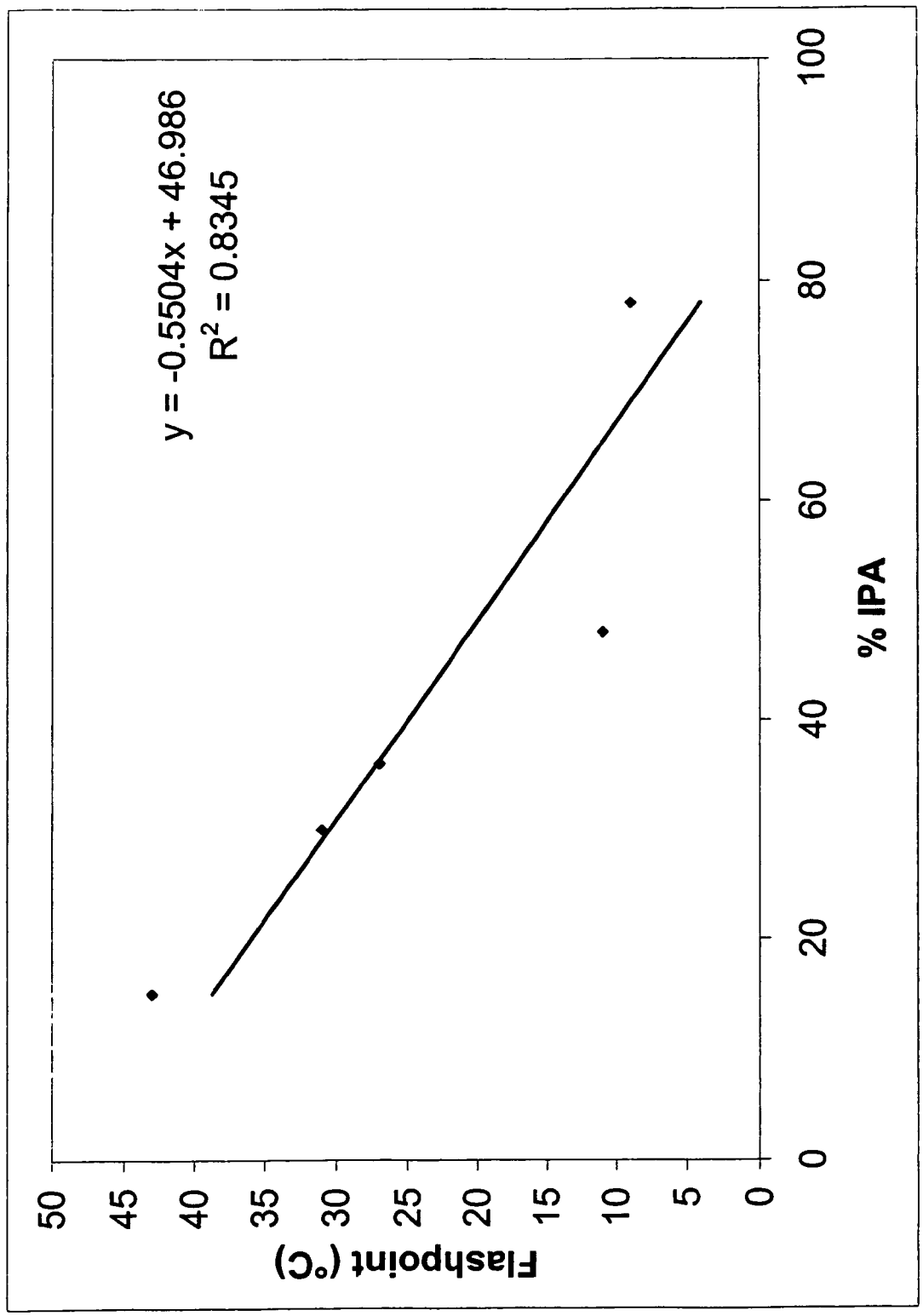
FIG. 3 depicts the correlation of the flash point of a mixture containing isopropyl alcohol and the % wt of isopropyl alcohol in the mixture.

The present invention provides a less-flammable gel formulation. In one embodiment, the formulation contains a mixture of organic solvent and isopropyl alcohol. The resulting mixture has a flash point that is higher than that of isopropyl alcohol (11.7° C.) alone. It has been determined that there is a correlation between an increase in flash point and the wt percentage of (% wt) isopropyl alcohol in the formulation (See, FIG. 3). Accordingly, mixing an organic solvent with isopropyl alcohol may increase flash point of the resulting mixture and render the formulation "less flammable" as a whole.

Accordingly, in one embodiment, the present invention provides a less-flammable gel formulation of malathion suitable for treating an ectoparasite in a mammal, comprising: a) about 0.5% by weight of malathion; b) at least one organic solvent selected from the group consisting of ethyl alcohol, isopropyl alcohol, propylene alcohol, benzyl alcohol, and propylene glycol; and c) hydroxylpropyl cellulose, such that the formulation has a flash point higher than that of the formulation containing 78% isopropyl alcohol (flash point=11.7° C.).

In another embodiment, the present invention provides a less-flammable gel gel formulation of malathion suitable for treating an ectoparasite in a mammal, comprising: a) about 0.5% by weight of malathion; b) at least one organic solvent selected from the group consisting of ethyl alcohol, isopropyl alcohol, propylene alcohol, benzyl alcohol, and propylene glycol; c) isopropyl myristate; and d) hydroxyl propyl cellulose, such that the formulation has a flash point higher than that of isopropyl alcohol (78% wt; flash point=11.7° C.).

In another yet embodiment, the present invention provides a less-flammable lotion formulation of malathion suitable for treating an ectoparasite in a mammal, comprising: a) about 0.1-10% by weight of malathion; and b) about 75% by weight of a mixture of isopropyl alcohol and at least one organic solvent selected from the group consisting of a glycol, and a $C_6$-$C_{12}$ triglyceride, wherein the organic solvent is at least about 35% by weight of the mixture.

Preferably, the less-flammable lotion formulation comprises about 0.25% to about 0.6% by weight of malathion. More preferably, the less-flammable lotion formulation comprises about 0.525% by weight of malathion.

Preferably, the less-flammable lotion formulation contains a glycol which is at least one solvent selected from propylene glycol, hexylene glycol, polypropylene glycol, or the like.

Preferably, the less-flammable lotion formulation contains about 48% by weight of glycol.

Preferably, the less-flammable lotion formulation contains propylene glycol. Preferably, the less-flammable lotion formulation contains hexylene glycol.

Preferably, the less-flammable lotion formulation contains about 38% by weight of a $C_6$-$C_{12}$ triglyceride. Preferably, the $C_6$-$C_{12}$ triglyceride is a $C_8$-$C_{10}$ triglyceride. More preferably, the formulation contains a mixture of isopropyl alcohol, a $C_8$ triglyceride and a $C_{10}$ triglyceride.

More preferably, the present invention provides a less-flammable lotion formulation of malathion suitable for treating an ectoparasite in a mammal, comprising: a) about 0.525% by weight of malathion; and b) about 40% by weight of isopropyl alcohol; and c) about 48% by weight of propylene glycol.

More preferably, the present invention provides a less-flammable lotion formulation of malathion suitable for treating an ectoparasite in a mammal, comprising: a) about 0.525% by weight of malathion; b) about 43% by weight of isopropyl alcohol; and c) about 38% by weight of a mixture of $C_8$ triglyceride and $C_{10}$ triglyceride.

In another embodiment, the present invention provides a process of preparing a topical gel pharmaceutical formulation of insecticide, comprising the steps of:
a) mixing a viscosity-modifying polymer in an organic solvent to hydrate the polymer in the organic solvent,
wherein the viscosity-modifying polymer is at least one polymer selected from the group consisting of a cellulosic polymer, acrylates, methacrylates, and polyvinyl pyrrolidone, wherein the organic solvent is selected from the group consisting of a lower alkyl alcohol, a ketone, a glycol and a mixture thereof,
wherein the organic solvent is at least about 75% by weight,
wherein the organic solvent contains at least about 40% by weight of the lower alkyl alcohol; and
b) adding about 0.1-10% by weight an insecticide into the polymer mixture to form a topical gel pharmaceutical formulation.

Preferably, the insecticide is an organophosphate. More preferably, the organophosphorous insecticide is malathion.

For purposes of the present invention, the ingredient malathion of the present pharmaceutical formulation is intended to encompass malathion having a purity of <99%, 99% (i.e., commercial source) (technical grade malathion) and malathion having a purity of >99% (pharmaceutical grade malathion). As stated, in a separate application (U.S. Provisional Application 60/697,010) entitled "Process for preparing pharmaceutical grade malathion" (filed Jul. 6, 2005), we have disclosed a novel and unique synthesis pathway for preparing a pharmaceutical grade malathion, which has an improved impurity profile, the disclosure of which is incorporated herein in its entirety. The pharmaceutical grade malathion has a purity of >99% and contains less than 0.1% isomalathion, 0.05% O,O,S-trimethyl phosphorothioate, and 0.1% methyl malathion.

In an embodiment, the improved pharmaceutical grade malathion contains the following impurity profile: <0.02% isomalathion, <0.04 wt % O,O,S-trimethyl phosphorothioate, and 0.08% methyl malathion. In addition, the improved pharmaceutical grade malathion contains <0.02% O,S,S,-trimethyl phosphorodithioate, 0.09% O,O,S-trimethyl phosphorodithioate, <0.05% malaoxon, 0.06% diethyl fumarate, <0.02% dimethyl malathion, 0.11% O,O-Me,Et malathion analog, and 0.08% tetraethyl dithiodisuccinate. The prepared pharmaceutical grade malathion may be conveniently and suitably used in the present gel pharmaceutical formulation.

Preferably, the mixing step (i.e., step a) is performed by heating and stirring. More preferably, the mixing step involves heating at about 45° C.

Preferably, the viscosity-modifying polymer is exemplified to include a cellulosic polymer and the like. Preferably, the cellulosic polymer is exemplified to include hydroxylethyl cellulose, hydroxy propyl cellulose, hydroxy propyl methyl cellulose, methyl cellulose, carboxy methyl cellulose, sodium carboxy methyl cellulose, ethyl cellulose and the like. More preferably, the cellulosic polymer is hydroxylpropyl cellulose.

Preferably, the organic solvent may include one or more solvent exemplified to include a lower alkyl alcohol, a ketone, a glycol and the like. More preferably, the lower alkyl alcohol is exemplified to include a $C_1$-$C_8$ alcohol and the like. More preferably, the lower alkyl alcohol is ethyl alcohol or isopropyl alcohol.

Preferably, the ketone is exemplified to include N-methylpyrrolidone, acetone and the like.

Preferably, the glycol is exemplified to include propylene glycol, hexylene glycol and the like.

Preferably, the process may further comprise the step of adding a fragrance. More preferably, the fragrance is least one compound exemplified to include terpineol, terpenes, pine needle oil, other natural and synthetic fragrances and the like.

Preferably, the process may further comprises the step of adding an antioxidant. More preferably, the antioxidant is at least one compound exemplified to include ascorbic acid, butylated hydroxyl anisole, butlylated hydroxy toluene, propyl gallate, tartaric acid, phosphoric acid, erythrobic acid, lactic acid, sodium sulfite, sodium bisulfate, sodium metabisulfite, thioglycolic acid, cysteine hydrochloride, alpha tocopherol and the like. Antioxidant may be present in salt forms. Preferably, the salt form of antioxidant is exemplified to include ascorbic acid, tartaric acid, phosphoric acid, erythrobic acid, lactic acid and the like.

In another embodiment, the present invention provides a method for treating an ectoparasite in a mammal, comprising the step of topically applying to a mammal a therapeutically effective amount of the topical gel pharmaceutical formulation, said formulation comprises: a) about 0.1-10% by weight of an insecticide; b) at least about 75% by weight of an organic solvent selected from the group consisting of a lower alkyl alcohol, a ketone, a glycol and a mixture thereof, wherein the organic solvent contains at least about 40% by weight of the lower alkyl alcohol; and c) at least one viscosity-modifying polymer selected from the group consisting of a cellulosic polymer, acrylates, methacrylates, and polyvinyl pyrrolidone.

In another embodiment, the present invention provides a method for treating an ectoparasite in a mammal, comprising the step of topically applying to a mammal a therapeutically effective amount of the topical gel pharmaceutical formulation, said formulation comprises: a) about 0.1-10% by weight of an insecticide; b) at least about 75% by weight of an organic solvent selected from the group consisting of a lower alkyl alcohol, a ketone, a glycol and a mixture thereof, wherein the organic solvent contains at least about 40% by weight of the lower alkyl alcohol; c) isopropyl myristate; and d) at least one viscosity-modifying polymer selected from the group consisting of a cellulosic polymer, acrylates, methacrylates, and polyvinyl pyrrolidone.

In another embodiment, the present invention provides a method for treating an ectoparasite in a mammal, comprising the step of topically applying to a mammal a therapeutically effective amount of the topical gel pharmaceutical formulation, said formulation comprises: a) about 0.5% by weight of malathion; b) at least about 75% by weight of an organic solvent selected from the group consisting of ethyl alcohol, isopropyl alcohol, benzyl alcohol, and propylene glycol, wherein the organic solvent contains at least about 40% by weight of ethyl alcohol or isopropyl alcohol; and c) hydroxyl propyl cellulose.

In another embodiment, the present invention provides a method for treating ectoparasites in a mammal, comprising the steps of: topically applying to a mammal a therapeutically effective amount of the topical gel pharmaceutical formulation, said gel pharmaceutical formulation comprises: malathion, ethyl alcohol and/or isopropyl alcohol, hydroxylpropyl cellulose. Optionally, the gel pharmaceutical formulation may contain isopropyl myristate. Optionally, the gel pharmaceutical formulation may also contain a fragrance and/or an antioxidant.

In another embodiment, the present invention provides a method for treating ectoparasites in a mammal, comprising the steps of: topically applying to a mammal a therapeutically effective amount of the topical gel pharmaceutical formulation, said gel pharmaceutical formulation comprises 0.5% by weight malathion, 78% by weight isopropyl alcohol, 1.0% by weight hydroxylpropyl cellulose. Optionally, the gel pharmaceutical formulation may contain 10% by weight dipentene, 10.1% by weight terpineol and 0.25% by weight pine needle oil.

Preferably, the present gel pharmaceutical formulation is highly effective in killing ectoparasites in a mammal. Preferably, the mammal is a human.

Preferably, the present pharmaceutical formulation of insecticide is a gel. Other suitable dosage forms include cream, foam and the like, insofar as the viscosity of these dosage forms is similar to that of the gel formulation.

Optionally, the present pharmaceutical formulation may be stored in a single compartment after the insecticide is mixed with the base formulation. Alternatively, the present pharmaceutical formulation may be stored in a multi-compartment dispensing system. For example, the insecticide may be stored in a first compartment; and the viscosity-modifying polymer in organic solvent (e.g., cellulosic polymer in isopropyl alcohol) may be conveniently stored in a second compartment. In accordance with the present invention, the first and second compartments may be separately stored. Preferably, the first and second compartments are stored under air-tight condition. Before use, a final composition is prepared by mixing the insecticide in the first compartment with the viscosity-modifying polymer in organic solvent (e.g., isopropyl alcohol) in the second compartment. Conveniently, the mixing of the individual compartments may occur in the dispensing system immediately prior to use. It is believed that such multi-compartment dispensing system avoid further possible degradation of insecticides (e.g., malathion) due to exposure to water and thus is believed to enhance the stability and shelf-life. Multi-compartment dispensing system may be stored without refrigeration.

The present gel pharmaceutical formulation is safe. Preferably, the gel pharmaceutical formulation is effective to kill head lice, body lice, pubic lice or treat scabies. Exemplified head lice include *Pediculis capitis* and the like. Exemplified body lice include *Pediculus humanus* and the like. Exemplified pubic lice include *Pthiris pubis* and the like. Exemplified scabies mite include *Sarcoptes scabiei* and the like.

Preferably, the gel pharmaceutical formulation is applied to the mammal for a time sufficient to kill the ectoparasites. Preferably, the topical gel is applied for about 15 minutes. Preferably, the topical gel is applied for about 30 minutes. Preferably, the topical gel is applied for about 60 minutes. Preferably, the topical gel is applied for about 90 minutes.

Preferably, the topical gel pharmaceutical formulation is applied so that the hair (or the body) is totally saturated with it. Preferably, the gel pharmaceutical formulation may be applied more than once, if required. Preferably, the gel pharmaceutical formulation may be applied a second time after 6 days to about 10 days after the first application. More preferably, the gel pharmaceutical formulation may be applied 7 days after the first application.

The present pharmaceutical formulation is in a gel form suitable for topical administration. The characteristics of the topical gel pharmaceutical composition allow the formulation to be applied with ease without dripping into eye, ear and neck or causing eye irritation along with a short application time. The present pharmaceutical formulation may encompass suitable dosage forms other than gel, such as cream or form, as long as they have similar viscosity as compared to that of the gel form.

The present topical gel pharmaceutical formulation is to be applied to totally saturate the scalp hair/the body. Preferably, the topical gel pharmaceutical formulation is applied to the hair/the body in the amount of about 50 grams. This will reduce the problem with current commercial compositions in which people are not sufficiently saturating their hair/the body with insecticide. By totally saturating the hair/the body, all the hair from the root to the tips will be inundated with the insecticide, and thereby eliminating the possibility of resistance developing.

The present topical gel pharmaceutical formulation may be applied for a short duration of time (e.g., 5 minutes to 2 hours) as compared to other commercial products instructed to have application time of 8-12 hours or overnight. The present topical gel pharmaceutical formulation is sufficient viscous enough to stay on the hair (or the body) but does not run off. The topical gel thus stays in contact with ectoparasites (such as lice and eggs) long enough to kill them.

Without wishing to be bound by theory, it is believed that the viscosity-modifying polymer provides a better vehicle to deliver an insecticide such as malathion so as to effectively kill the parasites such as head lice. It is further believed that the polymer provides an optimal viscosity, which permits sufficient exposure for the malathion to be exposed to the parasites. Head lice or scabies live on the surface of the scalp, the scalp hair and body respectively. The polymeric gel formulation provides a "depot" effect, keeping the insecticide on the surface of scalp, on the hair and the body by forming a thin film that washes away easily when rinsed with shampoo. This film allows insecticide to be in intimate contact with hair and body thus increasing the retention of the treatment on the hair and the outside surface of scalp and body. This reduces the absorption of treatment into the skin, which may cause neurotoxocity and which is a major disadvantage associated with some marketed products for treatment of head lice or scabies such as lindane shampoo.

Without further wishing to be bound by theory, the alkyl alcohol in the present formulation is maintained at an amount sufficient to effect the insecticide effect. Alkyl alcohol effects optimal killing of ectoparasites by serving as a vehicle to deliver the insecticide into the ectoparasite's body. Alkyl alcohol may provide osmotic force to dehydrate the ectoparasites and weaken them, rendering them more susceptible to the insecticide. Alkyl alcohol may also act synergistically with the insecticides in killing the ectoparasites.

Without further wishing to be bound by theory, it is believed that alkyl alcohol effects optimal killing of ectoparasites by opening up spiracles on the ectoparasites or opercula on their eggs and hence permits sufficient delivery of the insecticides.

The viscosity-modifying polymer, when prepared in a high alkyl alcohol solvent system (i.e., non-aqueous system), permits the gel to attain optimal viscosity to prevent easy runover of the formulation, which is in contrast to that of lotion where the run-over poses major disadvantages. The present gel formulation also prevents rapid evaporation of alkyl alcohol, which is found to be essential in ectoparasite killing.

Without further wishing to be bound by theory, it is believed that inclusion of isopropyl myristate may enhance the penetration of the insecticides (such as malathion) and provide effective killing of the ectoparasites.

The present invention is illustrated by means of the following examples representative of the pharmaceutical formulations included in the present invention, which should not be considered as restrictions of the scope of the same.

EXAMPLE 1

Topical Gel Pharmaceutical Formulation Containing Malathion

| INGREDIENTS | GEL FORMULA (% W/W) (Formulation No. 1) |
|---|---|
| Organophosphate (Malathion) | 0.525 |
| Hydroxy propyl cellulose (Klucel HF ®) | 1.0 |
| Fragrance | 0.5 |
| Isopropyl Alcohol | 48 |
| Propylene Glycol | 39.725 |
| Dipentene | — |
| Terpineol | 10 |
| Pine Needle Oil | 0.25 |

The formulation (example 1) was prepared in the following manner.
a) propylene glycol and isopropyl alcohol was mixed;
b) Klucel HF® was added to this solution and the mixture was stirred;
c) the mixture was heated to 45° C. and the temperature was maintained for 1 hour to allow the polymer to hydrate with continuous stirring;
d) the mixture was cooled to room temperature;
e) prepared terpineol (by warming to about 35° C. to melt) and added to the mixture;
f) malathion, fragrance & pine needle oil was weighed and dissolved in isopropyl alcohol (5%) (antioxidant, preservative may be added at this stage);
g) the dissolved malathion mixture (f) was added to terpineol mixture (e); and added to the mixture (d);
h) continued to mix for some time to achieve uniform distribution of drug and hydration of the polymer.

EXAMPLE 2

Topical Gel Pharmaceutical Formulation Containing Malathion

| INGREDIENTS | GEL FORMULA (% W/W) (Formulation No. 2) |
|---|---|
| Organophosphate (Malathion) | 0.525 |
| Hydroxy propyl cellulose (Klucel HF ®) | 1.0 |
| Fragrance | — |
| Isopropyl Alcohol | 78 |
| Propylene Glycol | — |
| Dipentene | 10 |
| Terpineol | 10.225 |
| Pine Needle Oil | 0.25 |

The formulation (example 2) was prepared in the following manner:
a) isopropyl alcohol was weighed
b) Klucel HF® was added and the mixture was stirred;
c) the mixture was heated to 45° C. and the temperature was maintained for 1 hour to allow the polymer to hydrate with continuous stirring;
d) the mixture was cooled to room temperature;
e) prepared Terpineol (by warming to about 35° C. to melt) and added to the mixture;
i) malathion, dipentene & pine needle oil were weighed and dissolved in isopropyl alcohol (5%) (antioxidant, preservative may be added at this stage);

f) the dissolved malathion mixture (f) was added to terpineol mixture (e); and added to the mixture (d);

g) continued to mix (g) for some time to achieve uniform distribution of drug and hydration of the polymer.

Without wishing to be bound by theory, it is believed that the amount of isopropyl alcohol, propylene glycol used in the pharmaceutical formulation may be varied so as to render the gel less flammable.

Alternatively limited amount of water or other solvents may be added to the formulation as illustrated in the following examples.

EXAMPLE 3

Further Topical Gel Formulations of Malathion: Gel Formulation

Several topical gel pharmaceutical formulations (#3-14) containing malathion were prepared and the respective ingredients are presented in Table 1. A combination of a variety of solvents, antioxidants, fragrance were prepared and evaluated for physical, chemical properties and their efficacy in killing lice in vitro. (See, Table 2).

EXAMPLE 4

Further Topical Gel Formulations of Malathion: Lotion Formulation

Additional topical pharmaceutical formulations (#15-22) containing malathion were prepared and the respective ingredients are presented in Table 3. The dosage form of these malathion formulations (differed from those in Example 3) was lotion. All of the tested formulations contain varying amount of solvents that exhibit less flammable activity (as compared to that of isopropyl alcohol). They contain a combination of a variety of solvents, antioxidants, and fragrances. The formulations 17, 18, 20, 21 and 22 were prepared in the following manner:

a) propylene glycol and 75% of the total amount of isopropyl alcohol were added to a container and stirred;

b) warmed Terpineol to 35° C. in a separate container and allowed to liquefy;

c) added Terpineol to solution of step a) with stirring;

d) added dissolved malathion, fragrance and pine needle oil (BHA and BHT, where mentioned) in about 10% of the total isopropyl alcohol;

e) added the solution in d) to mixture of c);

f) rinsed malathion container and Terpineol containers with remaining isopropyl alcohol and added rinsings to bulk solution of solution in c); and g) mixed for additional 30 minutes.

With respect to formulations #15 and 16, Miglyol was used (instead of propylene glycol) to mix with isopropyl alcohol.

With respect to formulation #19, Klucel HF was added in solution in step a) and warmed to 40° C. with stirring for 1 hour followed by cooling down to room temperature before step b) of warming Terpineol.

Lotion malathion formulations # 15-22 were evaluated for physical, chemical properties and their efficacy in killing lice in vitro. (See, Table 4). All of the tested malathion lotion formulations (except formulation #16) exhibited good in vitro lice killing activity, indicating that the less flammable formulations are equally effective as the Ovide® formulation. The stability data for formulations # 15-19 is shown in Tables 6A and 6B.

EXAMPLE 5

Topical Gel Formulation of Malathion Containing Isopropyl Myristate

Optionally, topical gel pharmaceutical formulation of malathion may contain isopropyl myristate. The following table illustrates such gel formulation (formulation #23).

| INGREDIENTS | GEL FORMULA (% W/W) (Formulation No. 23) |
|---|---|
| Organophosphate (Malathion) | 0.654 |
| Hydroxypropyl cellulose (Klucel HF ®) | 1.0 |
| Fragrance | 0.5 |
| Isopropyl Alcohol | 48 |
| Isopropyl Myristate | 10 |
| Propylene Glycol | 29.6 |
| Terpineol | 10.0 |
| Pine Needle Oil | 0.25 |

The formulation #23 (example 4) was prepared in the following manner:

a) propylene glycol and isopropyl alcohol (80% of total quantity required) were mixed;

b) Klucel HF was added and the mixture was stirred;

c) the mixture was then heated to and maintained at 40° C. for 1 hour to allow the polymer to hydrate with continuos stirring;

d) allowed the mixture to cool to room temperature;

e) prepared terpineol (by warming to about 35° C. to melt);

f) malathion, fragrance and pine needle oil were weighed and dissolved in isopropyl alcohol (10% of the total quantity required);

g) the dissolved malathion mixture and terpineol were added to the polymer mixture;

h) isopropyl myristate was weighed and added to the polymer mixture;

i) made up the weight of the mixture with remaining isopropyl alcohol and stirring for some more time to allow complete hydration of the polymer.

EXAMPLE 6

Viscosity Measurement

Physical property (i.e., viscosity) of the prepared topical gel pharmaceutical formulations was evaluated. The viscosity measurement was conducted using Brookfield viscometer (model No. RV DV III). The viscosity was measured at 50 rpm using Helipath spindle T-C at 25°. An average of five reading was calculated and was presented. The degree of variation among the readings was found to be minimal. The viscosity values are expressed in cps.

FIG. 1 depicts the viscosity values (expressed in cps) in a log scale. As shown in FIG. 1, all the gel formulations have viscosity values at least about 3,000 cps. Formulations 1 and 2 have viscosity values of about 5,000 cps. In comparison, Ovide® lotion, which is a liquid, has a low viscosity value of about 2 cps.

EXAMPLE 7

In Vitro Insecticide Activity

The prepared topical gel pharmaceutical formulations containing insecticide were evaluated for pediculicidal activity using an in vitro lice model. The prepared formulations are compared against several commercial products including Lindane Shampoo, Nix® cream rinse and Ovide® lotion.

The in vitro pediculicidal lice study was conducted as follow. Head lice (*Pediculus capitis*) were collected from the heads of infested human individuals. Ten lice, including male and female adults and nymphs were distributed evenly between test samples and control. The lice were placed in a sterile petri dish (15×60 mm) which contained five centimeter (5 cm) diameter cotton towel disks. The disks containing the test/control substance were dampened with filtered or distilled water to prevent dehydration of the cloth.

Lice specimens in each petri dish were examined with a 10× hand lens by the investigator for viability, intact legs and antennae. The following parameters were observed and recorded.

1) Behavior: Unsteady gait, stumbling, disorientation, convulsions, tremors, hyperexcitability and response to light, warmth and carbon dioxide.
2) Physical Signs: Bloating, dehydration, extrusion of gonads in males, excretion of blood meal, signs of peripheral nerve discharges, CNS toxicity, including tremors and twitching etc.
3) Incapacitation: Inability to walk, only occasional tremors or twitching of legs or antennae. This is a stage that lice rarely or never recover. At this stage they are described as moribund.
4) Death: When all movement of limbs, antennae and peristalsis of gut ceases. The definition of death in lice exposed to toxicants is difficult to determine. In many instances, individual lice may show no sign of life except an occasional twitch of an antenna or claw. Translated to a clinical situation, they are harmless, cannot feed, infest another person, or lay eggs.

Figure 2:
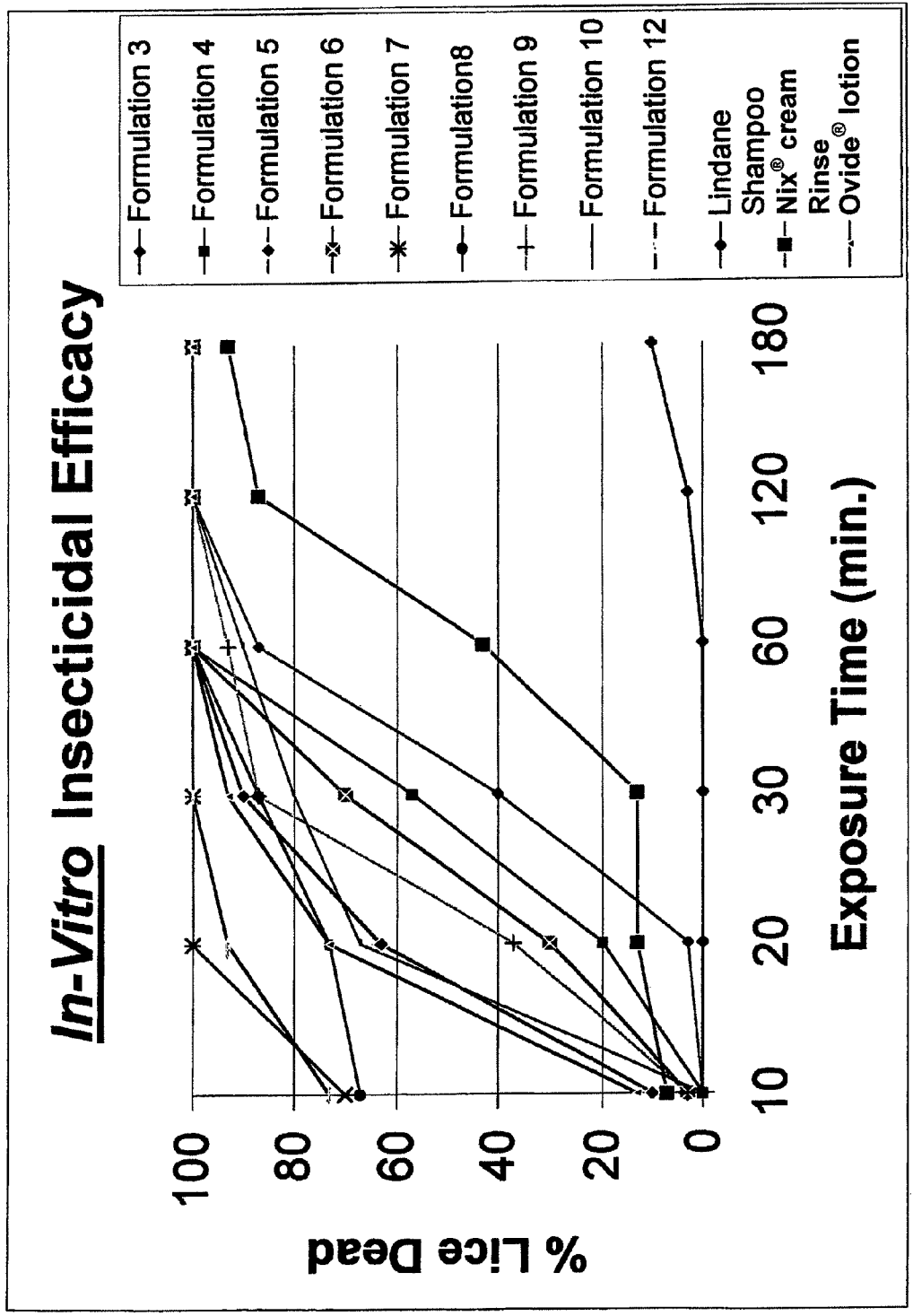
FIG. 2 depicts the in vitro efficacy of various gel formulations in killing lice.

These parameters were monitored up to 3 hours. The gel pharmaceutical formulations containing malathion showed excellent pediculicidal activity against head lice (*Pediculus capitis*). All the formulations exhibited 100% kill rate in one hour indicating the efficacy at shorter application time. As shown in FIG. 2, the present formulations (#3-12) exhibit good insecticide activity towards the head lice, reaching >80% killing activity by about 60 minutes. Note that the commercial pesticide preparations are less effective. While Nix® cream rinse reaches its 80% killing at about 120 minutes, the Lidane shampoo is totally ineffective during the 180 minutes period. The results are summarized in Table 2 for gel formulations and Table 4 for lotion formulations.

EXAMPLE 8

Stability Studies for Malathion Gel Formulations (Formulation # 1-14)

Stability of the topical gel pharmaceutical formulations was tested in stability chambers at various humidity and temperature conditions. The results are summarized in Tables 5A, 5B, 5C, 5D, 5E, 5F and 5G.

Various malathion gel formulations were evaluated at different conditions (i.e., 4° C., 25° C./60% relative humidity, 30° C./60% relative humidity and 40° C./75% relative humidity). The stability data indicate that the formulations are stable and meet the regulatory requirements.

EXAMPLE 9

Stability Studies for Malathion Lotion Formulations (Formulation # 15-22)

Stability of the topical lotion pharmaceutical formulations (containing less flammable solvents) was tested in humidity chambers at various conditions. The results are summarized in Tables 6A, and 6B.

Various malathion lotion formulations (containing less flammable solvents) were evaluated at different conditions (i.e., 4° C., 25° C./60% relative humidity, and 30° C./60% relative humidity). The stability data indicate that the formulations are stable at least for 3 months at 30° C./60% RH.

EXAMPLE 10

Stability Studies for Malathion Formulation Containing Isopropyl Myristate (Formulation # 23)

Stability of the topical gel pharmaceutical formulation (containing isopropyl myristate) was tested in humidity chambers at various conditions (i.e., 30° C./160% relative humidity, 40° C./75% relative humidity for 1-3 months). The results are summarized in Table 5G.

The stability data indicate that the formulation containing isopropyl myristate (formulation #23) has the similar stability profile as the formulations without isopropyl myristate (i.e., formulations # 1-14). Thus, optional addition of isopropyl myristate may enhance the efficacy of the formulation (e.g., by enhancing the penetration of malathion), without adversely affecting the stability of the gel formulation.

EXAMPLE 11

Further Topical Gel Formulations of Different Organophosphate Insecticides

Several topical gel pharmaceutical formulations (#24-28) containing various organophosphate were prepared and the respective ingredients are presented in following table.

| Formulation Nos. | Ingredients | Quantity (% w/w) (per 100 grams) | | | | |
|---|---|---|---|---|---|---|
| 24 | Phosmet | 0.6 | — | — | — | — |
| 25 | Parathion | — | 0.6 | — | — | — |
| 26 | Dioxathion | — | — | 0.6 | — | — |
| 27 | Terbufos | — | — | — | 0.6 | — |
| 28 | Prothiofos | — | — | — | — | 0.6 |
| 24-28 | Klucel HF ® | 1.0 | 1.0 | 1.0 | 1.0 | 1.0 |
| 24-28 | Isopropyl alcohol | 78 | 78 | 78 | 78 | 78 |
| 24-28 | Limonene | 10.0 | 10.0 | 10.0 | 10.0 | 10.0 |
| 24-28 | Pine Needle Oil | 0.25 | 0.25 | 0.25 | 0.25 | 0.25 |
| 24-28 | Terpineol | 10.096 | 10.096 | 10.096 | 10.096 | 10.096 |

The formulations #24-28 (example 11) was prepared in the following manner:
a) isopropyl alcohol (80% of total quantity required) was weighed;
b) Klucel HF® was added and the mixture was stirred;
c) the mixture was heated to 40° C. and the temperature was maintained for 1 hour to allow the polymer to hydrate with continuous stirring;
d) the mixture was cooled to room temperature;

e) prepared terpineol (by warming to about 35° C. to melt) and added to the mixture;
f) organophosphate insecticidal agent, limonene, fragrance and pine needle oil were weighed and dissolved in isopropyl alcohol (10% of the total quantity required);
g) the organophosphate insecticidal dissolved mixture and terpineol were added to the polymer mixture; and
h) made up the weight of the mixture remaining isopropyl alcohol and stirring for some more time to allow complete hydration of the polymer.

EXAMPLE 12

Physical Characterization of Formulations Containing Various Organophosphate Insecticidals The following table summarizes the physical characterization of various organophosphate gels.

| Physical Characteristics | Phosmet Gel | Parathion Gel | Dioxathion Gel | Terbufos Gel | Prothiofos Gel |
|---|---|---|---|---|---|
| Appearance | Colorless, slight hazy, pleasant smelling gel | Colorless, slight hazy, pleasant smelling gel | Colorless, slight hazy, pleasant smelling gel | Colorless, slight hazy, pleasant smelling gel | Colorless, slight hazy, pleasant smelling gel |
| Viscosity (cps) | 3,565 | 3,865 | 3,677 | 3,573 | 3,709 |

An evaluation of the physical characteristics of the prepared gel formulations containing various organophosphates indicates that these prepared gels share similar physical characteristics (e.g., appearance and viscosity). These data further support that other organophosphate insecticides similarly may be prepared in the gel formulation and share physical characteristics as well. Furthermore, it is reasonably to expect that they also exhibit similar in vitro and in vivo efficacy as that exhibited by malathion preparation.

EXAMPLE 13

Further Topical Gel Formulations of Different Insecticides

Several topical gel pharmaceutical formulations (#29-31) containing various insecticides were prepared and the respective ingredients are presented in following table.

| Formulation Nos. | Ingredients | Quantity (% w/w) (per 100 grams) | | |
|---|---|---|---|---|
| 29 | Piperonyl butoxide | 0.6 | — | — |
| 30 | Permethrin | — | 0.6 | — |
| 31 | Pyrethrin and pyrethroid | — | — | 0.6 |
| 29-31 | Klucel HF ® | 1.0 | 1.0 | 1.0 |
| 29-31 | Isopropyl alcohol | 78 | 78 | 78 |
| 29-31 | Limonene | 10.0 | 10.0 | 10.0 |
| 29-31 | Pine Needle Oil | 0.25 | 0.25 | 0.25 |
| 29-31 | Terpineol | 10.096 | 10.096 | 10.096 |

The formulations #29-31 (example 13) was prepared in the following manner:
a) isopropyl alcohol (80% of total quantity required) was weighed;
b) Klucel HF® was added and the mixture was stirred;
c) the mixture was heated to 40° C. and the temperature was maintained for 1 hour to allow the polymer to hydrate with continues stirring;
d) the mixture was cooled to room temperature;
e) prepared terpineol (by warming to about 35° C. to melt) and added to the mixture;
f) the insecticidal agent, limonene, fragrance and pine needle oil were weighed and dissolved in isopropyl alcohol (10% of the total quantity required);
g) the insecticidal dissolved mixture and terpineol were added to the polymer mixture; and
h) made up the weight of the mixture remaining isopropyl alcohol and stirring for some more time to allow complete hydration of the polymer.

EXAMPLE 14

Physical Characterization of Formulations Containing Different Insecticidals

The following table summarizes the physical characterization of different insecticidal gels.

| Physical Characteristics | Piperonyl butoxide Gel | Permethrin Gel | Pyrethrin and pyrethroid mixture Gel |
|---|---|---|---|
| Appearance | Colorless, slight hazy, pleasant smelling gel | Colorless, slight hazy, pleasant smelling gel | Colorless, slight hazy, pleasant smelling gel |
| Viscosity (cps) | 3,745 | 3,752 | 3,473 |

An evaluation of the physical characteristics of the prepared gel formulations containing different insecticides indicates that these prepared gels share similar physical characteristics (e.g., appearance and viscosity). These data further support that the different insecticides similarly may be prepared in the gel formulation and share physical characteristics as well. Furthermore, it is reasonable to expect that they also exhibit similar in vitro and in vivo efficacy as that exhibited by malathion preparation.

EXAMPLE 15

Clinical Studies

Clinical Protocol
The following clinical study was performed to compare the effectiveness and time of treatment for various malathion preparations. Specifically, one objective of the clinical study was to determine whether a 30-minute, 60 minute or 90 minute application of 0.5% malathion gel is as effective, or more effective, than the FDA approved 8-12 hour application of OVIDE® Lotion or the standard 10 minute application of NIX for the treatment of head lice. The 0.5% malathion gel composition (formulation no. 23) used in the clinical trial was:

| INGREDIENTS | GEL FORMULA (% W/W) (Formulation No. 23) |
|---|---|
| Organophosphate (Malathion) | 0.5 |
| Hydroxy propyl cellulose (Klucel HF ®) | 1.0 |
| Fragrance | — |
| Isopropyl Alcohol | 78 |
| Propylene Glycol | — |
| Dipentene | 10 |
| Terpineol | 10.1 |
| Pine Needle Oil | 0.25 |

Another objective of the clinical study was to determine the effects of various treatment times with the malathion gel (e.g., 30, 60 or 90 minutes) on the effectiveness of the malathion gel.

Study was performed in Florida, USA and participants were visually screened for the presence of live lice and viable nits. Inclusion criteria required a minimum of 3 live lice and 10 viable nits. Those family members who qualified for the study were asked to sign an informed consent after receiving an explanation of the procedures, risks, benefits and alternatives. Subjects were examined by the medical staff to ensure they met all other inclusion criteria.

A total of 174 subjects (mostly children) met the eligibility criteria and they were assigned a study number and randomized by household into one of five study groups:
1) 30 minute 0.5% malathion gel (Group A);
2) 60 minute 0.5% malathion gel (Group B);
3) 90 minute 0.5% malathion gel (Group C);
4) 8-12 hour OVIDE® treatment group (Group D); and
5) 10 minute application of NIX® Créme rinse (Group E).

Pediculicidal efficacy was established by the presence or absence of live lice. Ovicidal activity was assessed by visual examination of subjects with a lighted magnifier and also by the stage of nymphs or presence of adults at the 1 week and two week follow-ups.

All subjects were treated at Day 1. At Day 8 (±1), subjects were re-evaluated for efficacy. Anyone with live lice was retreated with the same product and time as Day 1. At Day 15 (±2 days), subjects did not receive treatment, but were shampooed, and examined. All subjects who were lice free at both Day 8 and 15, were considered a Treatment Success. Those who had live lice at Day 8, but not on Day 15, returned for a final follow up at Day 22 (±3) to determine if they were a Treatment Success or Failure.

The staff in charge of visual screening, informed consent, medical history and shampooing did not know to which group subjects were assigned. Similarly, the investigators that evaluated the safety and efficacy of subjects using test materials at the 1-week and 2-week visits, did not take part in the treatment applications and did not know which treatment was applied. Thus, this study was investigator blinded.

Data for each subject collected during the study period was entered into a case report form. Data from the case report form was statistically analyzed Results

| Study Subjects: Age | | |
|---|---|---|
| Age Group | Number of subjects | % |
| 2-6 | 50 | 29% |
| 7-12 | 70 | 41% |
| >12 | 51 | 30% |
| Total | 171 | 100% |

| Study Subjects: Gender Distribution | | | | | | |
|---|---|---|---|---|---|---|
| | A | B | C | D | E | Total |
| Male | 10 | 9 | 6 | 3 | 0 | 28 |
| % Male | 19% | 22% | 17% | 10% | 0% | 16% |
| Female | 43 | 32 | 29 | 26 | 13 | 143 |
| % Female | 81% | 78% | 83% | 90% | 100% | 84% |

Pediculicidal Efficacy

In the per protocol population there was a statistically significant difference between the overall success rate for each malathion gel treatment and that for NIX® (see "Overall Efficacy" Table below). Similar results were seen in the intention-to-treat population (with last observation carried forward) indicating that the exclusion of 10 patients with protocol violations did not alter the observed outcomes. When combining the three gel treatment groups (30, 60, and 90 min), the overall success rate was 97% in both the per protocol and intention-to-treat populations. The lower one-sided 90% confidence limits for the gel vs. OVIDE® differences were −7.4 (per protocol) and −7.0 (intention-to-treat).

| | A | | B | | C | | D | | E | |
|---|---|---|---|---|---|---|---|---|---|---|
| Overall Efficacy | | | % Success | | % Success | | % Success | | % Success | |
| | n | % Success (n) | N | (n) | n | (n) | n | (n) | n | (n) |
| One Treatment | 33 | 100% (33) | 24 | 92% (22) | 23 | 96% (22) | 19 | 100% (19) | 3 | 100% (3) |

-continued

Overall Efficacy

| | A<br>n | A<br>% Success (n) | B<br>N | B<br>% Success (n) | C<br>n | C<br>% Success (n) | D<br>n | D<br>% Success (n) | E<br>n | E<br>% Success (n) |
|---|---|---|---|---|---|---|---|---|---|---|
| Two Treatments | 19 | 95%* (18) | 16 | 100%* (16) | 9 | 100%* (9) | 9 | 100%* (9) | 7 | 29% (2) |
| Overall | 52 | 98%* (51) | 40 | 95%* (38) | 32 | 97%* (31) | 28 | 100%* (28) | 10 | 50% (5) |

*Statistically significant difference from NIX ® using Fishers exact test (two-sided).

Overall Efficacy (All gels combined)

| | All Gels N | All Gels % Succees (n) |
|---|---|---|
| One Treatment | 80 | 96% (77) |
| Two Treatments | 44 | 98% (43) |
| Overall | 124 | 97%* (120) |

*Statistically significant difference from NIX ® using Fishers exact test (two-sided).

Effect of Treatment Time

A comparison of the individual treatment groups shows that efficacy rates for the malathion gel were not significantly affected by treatment time. Efficacy rates were 98% for the 30-minute treatment, 95% for the 60-minute treatment and 97% for the 90-minute treatment. Each of these cure rates was statistically significantly superior to the NIX® control group. Based on these cure rates, it is conclude that treatment times of about 30 minutes is effective and 60 minute and 90 minute treatments achieve the same therapeutic efficacy.

Retreatment

On the second visit (Day 8) live lice were found on 35% ($^{44}/_{124}$) of the combined malathion gel subjects, 32% ($^{9}/_{28}$) of the OVIDE® subjects, and 70% ($^{7}/_{10}$) of the NIX® subjects. Using Fisher's exact test, the need for re-treatment rate for the combined gel group was significantly different from that of the NIX® group (p=0.0006) and not significantly different from that of the OVIDE® group.

At the end of 3 weeks 98% of the subjects ($^{51}/_{52}$) treated with a 0.5% malathion gel were lice free and 100% of subjects (28) treated with OVIDE® for eight hours were lice free. This result includes the subjects that received a second treatment.

In conclusion, the present clinical study clearly shows that a 30, 60, or 90-minute application of 0.5% malathion gel is highly effective in killing head lice (*Pediculus capitis*). Malathion gel is surprisingly found to be as effective as the eight hour treatment application for OVIDE®. The 98% cure rate of the 30-minute application of 0.5% malathion gel demonstrated that there is no statistically significant difference between the 0.5% malathion gel and the eight hour application of OVIDE®.

The disclosures of the cited publications are incorporated herein in their entireties by reference. It is to be understood, however, that the scope of the present invention is not to be limited to the specific embodiments described above. The invention may be practiced other than as particularly described and still be within the scope of the accompanying claims.

TABLE 1

Further Topical Gel Formulations (Formulation Nos. 3-14): Gel Formulations

| Ingredients | 3 | 4 | 5 | 6 | 7 | 8 | 9 | 10 | 11 | 12 | 13 | 14 |
|---|---|---|---|---|---|---|---|---|---|---|---|---|
| | % w/w (per 100 gm) | | | | | | | | | | | |
| Malathion | 0.525 | 0.525 | 0.525 | 0.525 | 0.525 | 0.525 | 0.525 | 0.525 | 0.525 | 0.525 | 0.525 | 0.525 |
| Klucel HF ® | 1.0 | 1.0 | 1.0 | 1.0 | 1.0 | 1.0 | 1.0 | 1.0 | 1.0 | 1.0 | 1.0 | 1.0 |
| Fragrance | 0.5 | 0.5 | 0.5 | 0.5 | 0.5 | 0.5 | 0.5 | 0.5 | — | — | 0.5 | 0.5 |
| Benzyl Alcohol | 5.0 | 5.0 | 5.0 | 5.0 | — | — | 5.0 | 5.0 | — | — | 5.0 | |
| Ethyl Alcohol | 20.0 | 40 | 20 | — | — | — | 20 | — | — | — | 20 | |
| Isopropyl alcohol | — | — | 20 | 40 | 78 | 78 | 25 | 25 | 78.0 | 78.0 | 20 | 78 |
| Propylene Glycol | 72.975 | 52.975 | 52.975 | 52.975 | 19.9775 | — | 47.775 | 47.775 | — | — | 52.911 | 19.911 |
| BHA | — | — | — | — | 0.1 | 0.1 | 0.1 | 0.1 | — | 0.1 | — | — |
| BHT | — | — | — | — | 0.1 | 0.1 | 0.1 | 0.1 | — | 0.1 | — | — |
| N-Methyl-2Pyrrolidone | — | — | — | — | — | 19.775 | — | 20 | — | — | — | — |
| Limonene | — | — | — | — | — | — | — | — | 10.0 | 10 | — | — |
| Terpineol | — | — | — | — | — | — | — | — | 10.225 | 10.025 | — | — |
| Pine needle oil | — | — | — | — | — | — | — | — | 0.25 | 0.28 | — | — |
| Tocopherol | | | | | | | | | | | 0.064 | 0.064 |

TABLE 2

In Vitro Insecticide Activity (Lice Killing Model)

% Lice Dead

| Exposure Time | Topical Gel Formulation No. 3 | Topical Gel Formulation No. 4 | Topical Gel Formulation No. 5 | Topical Gel Formulation No. 6 | Topical Gel Formulation No. 7 | Topical Gel Formulation No. 8 | Topical Gel Formulation No. 9 | Topical Gel Formulation No. 10 | Topical Gel Formulation No. 12 | Lindane ® Shampoo | Nix ® Cream Rinse | OVIDE ® Lotion |
|---|---|---|---|---|---|---|---|---|---|---|---|---|
| 10 min | 0 | 0 | 10 | 3 | 70 | 67 | 3 | 0 | 73 | 0 | 7 | 13 |
| 20 min | 3 | 20 | 63 | 30 | 100 | 73 | 37 | 67 | 93 | 0 | 13 | 73 |
| 30 min | 40 | 57 | 90 | 70 | 100 | 87 | 87 | 80 | 100 | 0 | 13 | 93 |
| 1 Hour | 87 | 100 | 100 | 100 | 100 | 100 | 93 | 90 | 100 | 0 | 43 | 100 |
| 2 Hour | 100 | 100 | 100 | 100 | 100 | 100 | 100 | 100 | 100 | 3 | 87 | 100 |
| 3 Hour | 100 | 100 | 100 | 100 | 100 | 100 | 100 | 100 | 100 | 10 | 93 | 100 |

TABLE 3

Additional Topical Formulations (Formulation Nos. 15-22): Lotion Formulations

| Ingredients | 15 | 16 | 17 | 18 | 19 | 20 | 21 | 22 | Ovide ® |
|---|---|---|---|---|---|---|---|---|---|
| | | | | % w/w (for 100 gm) | | | | | |
| Malathion | 0.525 | 0.525 | 0.525 | 0.525 | 0.525 | 0.525 | 0.525 | 0.525 | 0.525 (w/v) |
| Klucel HF | — | — | — | — | 0.25 | — | — | — | — |
| Fragrance | — | — | — | 0.5 | 0.5 | 0.5 | 0.5 | 0.5 | — |
| Isopropyl alcohol | 43 | — | 40.6 | 40 | 40 | 40 | 40 | 40 | 78.32 (v/v) |
| Propylene Glycol | — | — | 48.63 | 48.725 | 48.475 | 48.625 | 48.625 | 48.525 | — |
| BHA | — | — | — | — | — | 0.1 | — | 0.1 | — |
| BHT | — | — | — | — | — | — | 0.1 | 0.1 | — |
| Miglyol | 38.23 | 81.23 | — | — | — | — | — | — | — |
| Terpineol | 10.0 | 10 | 10 | 10 | 10 | 10 | 10 | 10 | 11.0 (v/v) |
| Limonene | 8.0 | 8 | — | — | — | — | — | — | 10.0 (v/v) |
| Pine needle Oil | 0.25 | 0.25 | 0.25 | 0.25 | 0.25 | 0.25 | 0.25 | 0.25 | 0.25 (v/v) |

TABLE 4

In Vitro Insecticide Activity (Lice Killing Model)

Malathion Lotion Formulations

| Exposure Time | #15 % Lice Dead | #16 % Lice Dead | #17 % Lice Dead | #18 % Lice Dead | #19 % Lice Dead | Ovide ® % Lice Dead | Ovide ® % Lice Dead |
|---|---|---|---|---|---|---|---|
| 10 min | 40 | 0 | 0 | 0 | 0 | 0 | 13 |
| 20 min | 47 | 0 | 30 | 7 | 20 | 97 | 73 |
| 30 min | 57 | 0 | 100 | 40 | 70 | 100 | 93 |
| 1 Hour | 70 | 0 | 100 | 100 | 100 | 100 | 100 |
| 2 Hour | 73 | 7 | 100 | 100 | 100 | 100 | 100 |
| 3 Hour | 87 | 30 | 100 | 100 | 100 | 100 | 100 |

TABLE 5A

Stability of Topical Gel Pharmaceutical Formulation Containing Organophosphate (Malathion)

| | Stability | | Formulation Nos. | | | |
|---|---|---|---|---|---|---|
| | Condition | Time | 3 | 4 | 5 | 6 |
| Description | Initial | | Slight Hazy color less viscous gel | Slight Hazy color less viscous gel | Slight Hazy colorless viscous gel | Slight Hazy color less viscous gel |
| | 4° C. | 3 M | NC | NC | NC | NC |
| | 25° C. | 3 M | NC | NC | NC | NC |
| | 30° C. | A. | NC | NC | NC | NC |
| | 30° C. | B. | NC | NC | NC | NC |
| | 30° C. | C. | NC | NC | NC | NC |
| Assay (%) | Initial | | 106.25 | 107.6 | 105.9 | 104.2 |
| | 4° C. | 3 M | 103.7 | 103.8 | 104.7 | 102.3 |
| | 25° C. | 3 M | 96.45 | 97.5 | 98.45 | 95.7 |
| | 30° C. | 1 M | 96.65 | 98.85 | 100.1 | 97.35 |
| | 30° C. | 2 M | 95.1 | 94.3 | 94.2 | 94.8 |
| | 30° C. | 3 M | 91.1 | 90.55 | 92.7 | 91.1 |

TABLE 5A-continued

Stability of Topical Gel Pharmaceutical Formulation Containing Organophosphate (Malathion)

| | Stability Condition | Time | Formulation Nos. | | | |
|---|---|---|---|---|---|---|
| | | | 3 | 4 | 5 | 6 |
| Viscosity | Initial | | 5296 | 3412 | 3608 | 4064 |
| | 25° C. | 3 M | 5176 | 3164 | 3612 | 3840 |
| | 30° C. | 1 M | 4952 | 3200 | 3676 | 4060 |
| | 30° C. | 2 M | 5172 | 3212 | 3496 | 4028 |
| | 30° C. | 3 M | 4712 | 3140 | 3448 | 3604 |

NC—No Change
M represents month(s)
A represents 1 month;
B represents 2 months; and
C represents 3 months

TABLE 5B

Stability of Topical Gel Pharmaceutical Formulation Containing Organophosphate (Malathion)

| Parameter | Stability Condition | Time | Formulation Nos. | | | |
|---|---|---|---|---|---|---|
| | | | 7 | 8 | 9 | 10 |
| Description | Initial | | Slight Hazy color less viscous gel | Slight Hazy color less viscous gel | Slight Hazy color less viscous gel | Slight Hazy color less viscous gel |
| | 4° C. | 3 M | NC | NC | NC | NC |
| | 25° C. | 3 M | NC | NC | NC | NC |
| | 30° C. | D. | NC | NC | NC | NC |
| | 30° C. | E. | NC | NC | NC | NC |
| | 30° C. | F. | NC | NC | NC | NC |
| Assay (%) | Initial | | 106.2 | 105.6 | 102.6 | 100.2 |
| | 4° C. | 3 M | 106.53 | 105.1 | 105 | 101.13 |
| | 25° C. | 3 M | 106.7 | 101.5 | 100.8 | 95.1 |
| | 30° C. | 1 M | 99.8 | 98.4 | 98.8 | 93.3 |
| | 30° C. | 2 M | NA | 96.65 | 99.6 | 92.25 |
| | 30° C. | 3 M | NA | 102.1 | 99.4 | NA |
| Viscosity | Initial | | 2916 | 2260 | 3228 | 3592 |
| | 4° C. | 3 M | 2824 | 2228 | 3204 | 3696 |
| | 25° C. | 3 M | 2964 | 2316 | 3289 | 4048 |
| | 30° C. | 1 M | 2940 | 2204 | 3556 | 3820 |
| | 30° C. | 2 M | 3380 | 2264 | 3220 | 3800 |
| | 30° C. | 3 M | 3324 | 2404 | 3212 | 4312 |

NC—No Change
NA—Not analyzed
D represents 1 month;
E represents 2 months; and
F represents 3 months

TABLE 5C

Stability of Topical Gel Pharmaceutical Formulation Containing Organophosphate (Malathion)

| Parameter | Stability Condition | Time | Formulation No. | |
|---|---|---|---|---|
| | | | 11 | 12 |
| Description | Initial | | Slight Hazy color less viscous gel | Slight Hazy color less viscous gel |
| | 4° C. | 3 M | NC | NC |
| | 25° C. | 3 M | NC | NC |
| | 30° C. | G. | NC | NC |
| | 30° C. | H. | NC | NC |
| | 30° C. | I. | NC | NC |
| | 40° C. | 1 M | NC | NC |
| | 40° C. | 2 M | NC | NC |
| | 40° C. | 3 M | NC | NC |
| Assay (%) | Initial | | 105.2 | 107.4 |
| | 4° C. | 3 M | 109.0 | 110.03 |
| | 25° C. | 3 M | 105.7 | 107.9 |
| | 25° C. | 6 M | 104.87 | |
| | 30° C. | 1 M | 105.8 | 108.75 |
| | 30° C. | 2 M | 109.1 | 108.85 |
| | 30° C. | 3 M | 104.5 | 107.7 |
| | 30° C. | 6 M | 101.90 | NA |
| | 40° C. | 1 M | 97.7 | 103 |
| | 40° C. | 2 M | 95.65 | NA |
| | 40° C. | 3 M | 93.5 | 95.27 |
| Content of Isopropyl Alcohol (%) | 4° C. | 3 M | 98.4 | NA |
| | 30° C. | 3 M | 95.5 | NA |
| | 40° C. | 3 M | 96.4 | NA |

NC—No Change
NA—Not Analyzed
G represents 1 month;
H represents 2 months;
and I represents 3 months

TABLE 5D

Stability of Topical Gel Pharmaceutical Formulation Containing Organophosophate (Malathion)

| Parameter | Stability Condition | Time | Formulation No. 14 |
|---|---|---|---|
| Description | Initial | | Slight Hazy color less viscous gel |
| | 25° C. | 3 M | NC |
| | 30° C. | J. | NC |
| | 30° C. | K. | NC |
| | 30° C. | L. | NC |
| | 40° C. | 1 M | NC |
| | 40° C. | 2 M | NC |
| | 40° C. | 3 M | NC |
| Assay (%) | Initial | | 104.8 |
| | 25° C. | 3 M | 97.5 |
| | 30° C. | 1 M | 105.6 |
| | 30° C. | 2 M | 100.6 |
| | 30° C. | 3 M | 95.9 |
| | 40° C. | 1 M | 100.9 |
| | 40° C. | 2 M | 94.7 |
| | 40° C. | 3 M | 93.0 |
| Viscosity | Initial | | 3060 |
| | 25° C. | 3 M | 4376 |
| | 30° C. | 1 M | 2960 |
| | 30° C. | 2 M | 3084 |
| | 30° C. | 3 M | 4404 |
| | 40° C. | 1 M | 3044 |
| | 40° C. | 2 M | 3128 |
| | 40° C. | 3 M | 4352 |

NC—No Change
J represents 1 month;
K represents 2 months;
end L represents 3 months

TABLE 5E

Stability of Topical Gel Pharmaceutical Formulation Containing Organophosphate (Malathion)

| Parameter | Stability Condition | Time | Formulation No. 1 |
|---|---|---|---|
| Description | Initial | | Slight Hazy, colorless, viscous gel |
| | 25° C. | 3 M | NC |
| | 30° C. | M. | NC |
| | 30° C. | N. | NC |
| | 30° C. | O. | NC |
| Assay (%) | Initial | | 103.9 |
| | 25° C. | 3 M | 101.2 |
| | 30° C. | 1 M | 102.9 |
| | 30° C. | 2 M | 105.53 |
| | 30° C. | 3 M | 101.8 |
| Viscosity | Initial | | 5225 |
| | 25° C. | 3 M | 4540 |
| | 30° C. | 1 M | 4378 |
| | 30° C. | 2 M | 4092 |
| | 30° C. | 3 M | 3660 |
| Content of Isopropyl alcohol (%) | 4° C. | 3 M | 98.9 |
| | 25° C. | 3 M | 96.7 |
| | 30° C. | 3 M | 96.6 |

NC—No Change
M represents 1 month;
N represents 2 months; and
O represents 3 months

TABLE 5F

Stability of Topical Gel Pharmaceutical Formulation Containing Organophosphate (Malathion)

| Parameter | Stability Condition | Time | Formulation No. 2 |
|---|---|---|---|
| Description | Initial | | Slight Hazy color less viscous gel |
| | 25° C. | 3 M | NC |
| | 30° C. | P. | NC |
| | 30° C. | Q. | NC |
| | 30° C. | R. | NC |
| | 40° C. | 1 M | NC |
| | 40° C. | 2 M | Light yellow, viscous gel |
| | 40° C. | 3 M | Yellow, viscous gel |
| Assay (%) | Initial | | 104.15 |
| | 25° C. | 3 M | 103.05 |
| | 30° C. | 1 M | 103.1 |
| | 30° C. | 2 M | 102.3 |
| | 30° C. | 3 M | 100.21 |
| | 40° C. | 1 M | 99.7 |
| | 40° C. | 2 M | 97.24 |
| | 40° C. | 3 M | 94.38 |
| Content of Isopropyl Alcohol (%) | 4° C. | 1 M | 99.0 |
| | 30° C. | 1 M | 97.8 |
| | 40° C. | 1 M | 96.0 |

NC—No Change
P represents 1 month;
Q represents 2 months; and
R represents 3 months

TABLE 5G

Stability of Topical Gel Pharmaceutical Formulation Containing Isopropyl Myristate

| Parameter | Stability Condition | Time | Formulation No. 23 |
|---|---|---|---|
| Description | Initial | | Slight Hazy color less viscous gel with pleasant smell |
| | 30° C. | 1 M | Slight Hazy color less viscous gel with pleasant smell |
| | 30° C. | 2 M | Slight Hazy color less viscous gel with pleasant smell |
| | 30° C. | 3 M | Sample on stability |
| | 40° C. | 1 M | Slight Hazy color less viscous gel with pleasant smell |
| | 40° C. | 2 M | Slight Hazy color less viscous gel with pleasant smell |
| | 40° C. | 3 M | Sample on stability |
| Assay (%) | Initial | | 107.48 |
| | 30° C. | 1 M | 105.87 |
| | 30° C. | 2 M | 105.66 |
| | 30° C. | 3 M | Sample on stability |
| | 40° C. | 1 M | 102.67 |
| | 40° C. | 2 M | 100.02 |
| | 40° C. | 3 M | Sample on stability |
| Viscosity (cps) | Initial | | 4,477 |
| | 30° C. | 1 M | 4,896 |
| | 30° C. | 2 M | 4,931 |
| | 30° C. | 3 M | Sample on stability |
| | 40° C. | 1 M | 4,067 |
| | 40° C. | 2 M | 3,844 |
| | 40° C. | 3 M | Sample on stability |
| IPA content (%) | Initial | | 99.05 |
| | 30° C. | 1 M | 98.65 |
| | 30° C. | 2 M | 97.9 |
| | 30° C. | 3 M | Sample on stability |
| | 40° C. | 1 M | 96.3 |
| | 40° C. | 2 M | 96.6 |
| | 40° C. | 3 M | Sample on stability |

TABLE 6A

Stability of Topical Lotion Formulations Containing Organophosphate (Malathion)

| Parameter | Stability Condition | Time | Formulation Nos. 15 | 16 | 17 |
|---|---|---|---|---|---|
| Description | Initial | | Pale yellow colored, clear, solution | Pale yellow colored, clear, solution | Clear, colorless, solution |
| | 4° C. | | NC | NC | NC |
| | 4° C. | 3 M | NC | NC | NC |
| | 25° C. | 3 M | NC | NC | NC |
| | 30° C. | S. 1 M | NC | NC | NC |
| | 30° C. | T. 2 M | NC | NC | NC |
| | 30° C. | U. 3 M | NC | NC | NC |
| Assay (mg/g) | Initial | | 106.8 | 105.6 | 105.8 |
| | 4° C. | 1 M | 104.9 | 102.1 | 104.1 |
| | 4° C. | 3 M | 101.8 | 98.6 | 102.7 |
| | 25° C. | 3 M | 101.2 | 98.8 | 100.5 |
| | 30° C. | 1 M | 103.5 | 102.2 | 101.0 |
| | 30° C. | 2 M | 106.95 | 104.75 | 102.8 |
| | 30° C. | 3 M | 101 | 99 | 97.8 |

NC—No change

TABLE 6B

Stability of Topical Lotion Formulations Containing Organophosphate (Malathion)

| Parameter | Stability Condition | Time | Formulation Nos. 18 | 19 |
|---|---|---|---|---|
| Description | Initial | | Pale yellow colored, clear, solution | Pale yellow colored, clear, solution |
| | 4° C. | | NC | NC |
| | 30° C. | V. 1 M | NC | NC |
| | 30° C. | W. 2 M | NC | NC |
| | 30° C. | X. 3 M | NC | NC |
| Assay (mg/g) | Initial | | 105.52 | 106.5 |
| | 25° C. | 3 M | 104 | 104.1 |
| | 30° C. | 1 M | 104 | 104.8 |
| | 30° C. | 2 M | 98.3 | 99.3 |
| | 30° C. | 3 M | 99.6 | 99.5 |

NC—No change

What is claimed is:

1. A less-flammable lotion formulation of malathion suitable for treating an ectoparasite in a mammal, consisting of:
   a) about 0.1-10% by weight of malathion;
   b) greater than about 75% by weight of a mixture of isopropyl alcohol and at least one organic solvent selected from the group consisting of a glycol, and a $C_6$-$C_{12}$ triglyceride, wherein the organic solvent is at least about 35% by weight of the formulation;
   c) optionally at least one of terpineol, dipentene, limonene, and/or pine needle oil; and
   d) optionally at least one antioxidant.

2. The less-flammable lotion formulation of claim 1, wherein the formulation contains about 0.25% to about 0.6% by weight of malathion.

3. The less-flammable lotion formulation of claim 1, wherein the formulation contains about 0.525% by weight of malathion.

4. The less-flammable lotion formulation of claim 1, wherein the glycol is at least one solvent selected from the group consisting of propylene glycol, hexylene glycol, and polypropylene glycol.

5. The less-flammable lotion formulation of claim 1, wherein the formulation contains about 48% by weight of glycol.

6. The less-flammable lotion formulation of claim 1, wherein the glycol is propylene glycol.

7. The less-flammable lotion formulation of claim 1, wherein the glycol is hexylene glycol.

8. The less-flammable lotion formulation of claim 1, wherein the organic solvent consists of about 38% by weight of $C_6$-$C_{12}$ triglyceride.

9. The less-flammable lotion formulation of claim 1, wherein the $C_6$-$C_{12}$ triglyceride is a $C_8$-$C_{10}$ triglyceride.

10. The less-flammable lotion formulation of claim 1, wherein the formulation contains a mixture of isopropyl alcohol, a $C_8$ triglyceride and a $C_{10}$ triglyceride.

11. The lotion according to claim 1, including at least one of terpineol, dipentene, limonene, and/or pine needle oil.

12. The lotion according to claim 1, including at least one antioxidant.

13. The lotion according to claim 12, wherein the antioxidant is BHA or BHT.

14. The less-flammable lotion formulation of claim 1 consisting of:
   a) about 0.525% by weight of malathion;
   b) about 40% by weight of isopropyl alcohol;
   c) about 48% by weight of propylene glycol;
   d) optionally at least one of terpineol, dipentene, limonene, and/or pine needle oil; and
   e) optionally at least one antioxidant.

15. The less-flammable lotion formulation of claim 1 consisting of:
   a) about 0.525% by weight of malathion;
   b) about 43% by weight of isopropyl alcohol;
   c) about 38% by weight of a mixture of $C_8$ triglyceride and $C_{10}$ triglyceride;
   d) optionally at least one of terpineol, dipentene, limonene, and/or pine needle oil; and
   e) optionally at least one antioxidant.

16. A lotion formulation of malathion suitable for treating an ectoparasite in a mammal, consisting of:

a) an active agent consisting of about 0.1-10% by weight of malathion; and
b) a vehicle consisting of a mixture of isopropyl alcohol and at least one organic solvent selected from the group consisting of a glycol and a $C_6$-$C_{12}$ triglyceride, where the organic solvent is at least about 35% by weight of the formulation;
d) optionally at least one of terpineol, dipentene, limonene, and/or pine needle oil; and
e) optionally at least one antioxidant.

17. The lotion according to claim 16, including at least one of terpineol, dipentene, limonene, and/or pine needle oil.

* * * * *